US011896310B2

(12) United States Patent
Tokuda et al.

(10) Patent No.: US 11,896,310 B2
(45) Date of Patent: Feb. 13, 2024

(54) OPHTHALMOLOGIC INFORMATION PROCESSING APPARATUS, OPHTHALMOLOGIC SYSTEM, OPHTHALMOLOGIC INFORMATION PROCESSING METHOD, AND RECORDING MEDIUM

(71) Applicant: TOPCON CORPORATION, Tokyo (JP)

(72) Inventors: Kanichi Tokuda, Saitama (JP); Taiki Aimi, Musashino (JP)

(73) Assignee: TOPCON CORPORATION, Tokyo (JP)

( * ) Notice: Subject to any disclaimer, the term of this patent is extended or adjusted under 35 U.S.C. 154(b) by 583 days.

(21) Appl. No.: 16/878,625

(22) Filed: May 20, 2020

(65) Prior Publication Data
US 2020/0281464 A1    Sep. 10, 2020

Related U.S. Application Data

(63) Continuation of application No. PCT/JP2018/038118, filed on Oct. 12, 2018.

(30) Foreign Application Priority Data

Nov. 24, 2017    (JP) ................................ 2017-225876

(51) Int. Cl.
    *A61B 3/10*    (2006.01)
    *A61B 3/12*    (2006.01)
    (Continued)

(52) U.S. Cl.
    CPC .............. *A61B 3/12* (2013.01); *A61B 3/0041* (2013.01); *A61B 3/102* (2013.01); *A61B 3/14* (2013.01);
    (Continued)

(58) Field of Classification Search
    CPC ........... A61B 3/103; A61B 3/14; A61B 3/152; A61B 3/1225; A61B 3/024; A61B 3/1015;
    (Continued)

(56) References Cited

U.S. PATENT DOCUMENTS

2007/0115481 A1    5/2007    Toth et al.
2009/0161827 A1*   6/2009    Gertner ................ A61N 5/1017
                                                     378/65
(Continued)

FOREIGN PATENT DOCUMENTS

EP    2896355 A1    7/2015
EP    3054420 A2    8/2016
(Continued)

OTHER PUBLICATIONS

Japanese Office Action dated May 24, 2022, in Japanese Application No. 2021-111860.
(Continued)

*Primary Examiner* — Dawayne Pinkney
(74) *Attorney, Agent, or Firm* — XSENSUS LLP

(57) ABSTRACT

An ophthalmologic information processing apparatus includes an analyzer, a storage unit, and a display controller. The analyzer is configured to specify an atrophy region in a fundus by analyzing data of the fundus of a subject's eye acquired using optical coherence tomography. The storage unit stores image data of the fundus. The display controller is configured to cause a fundus image of the subject's eye to be displayed on a display means based on the image data stored in the storage unit, and to cause a region corresponding to the atrophy region in the fundus image to be displayed on the display means so as to be identifiable.

21 Claims, 14 Drawing Sheets

(51) Int. Cl.
*A61B 3/02* (2006.01)
*G06T 7/11* (2017.01)
*A61B 3/00* (2006.01)
*A61B 3/14* (2006.01)

(52) U.S. Cl.
CPC ...... *G06T 7/11* (2017.01); *G06T 2207/10101* (2013.01); *G06T 2207/30041* (2013.01)

(58) Field of Classification Search
CPC ..... A61B 3/0025; A61B 3/102; A61B 5/0066; G01N 2021/1787; G01N 21/4795; G06T 7/0012; G06T 2207/10101; G06T 2207/30041
USPC ....... 351/206, 200, 205, 208–210, 221, 222, 351/246
See application file for complete search history.

(56) References Cited

U.S. PATENT DOCUMENTS

| | | |
|---|---|---|
| 2012/0194783 A1 | 8/2012 | Wei et al. |
| 2013/0188135 A1 | 7/2013 | Iwase et al. |
| 2014/0018676 A1* | 1/2014 | Kong ........................ A61B 8/08 600/438 |
| 2014/0152957 A1 | 6/2014 | Reisman et al. |
| 2015/0201829 A1 | 7/2015 | Yang et al. |
| 2015/0366448 A1 | 12/2015 | Iwase et al. |
| 2016/0206190 A1 | 7/2016 | Reisman et al. |
| 2016/0284103 A1* | 9/2016 | Huang ..................... G01B 11/00 |
| 2017/0065163 A1 | 3/2017 | Yang et al. |
| 2017/0316567 A1* | 11/2017 | Kotoku ..................... G06T 7/11 |
| 2018/0003479 A1* | 1/2018 | Tomatsu ................ G06V 10/44 |
| 2019/0347796 A1 | 11/2019 | Huang |

FOREIGN PATENT DOCUMENTS

| | | |
|---|---|---|
| JP | 2008-295804 A | 12/2008 |
| JP | 2010-268916 A | 12/2010 |
| JP | 2013-165953 A | 8/2013 |
| JP | 2014-505552 A | 3/2014 |
| JP | 2014-108351 A | 6/2014 |
| JP | 2015-136626 A | 7/2015 |
| JP | 2016-107148 A | 6/2016 |
| WO | 2016/153877 A1 | 9/2016 |

OTHER PUBLICATIONS

Extended European search report dated Jul. 1, 2021, in corresponding European patent Application No. 18880778.8, 8 pages.
International Search Report and Written Opinion dated Dec. 11, 2018 for PCT/JP2018/038118 filed on Oct. 12, 2018, 12 pages including English Translation of the International Search Report.
Kanji, T., et al., "Guideline Diagnostic Criteria for Atrophic Age related Macular Degeneration," Journal of Japanese Ophthalmological Society, vol. 119, No. 10, Oct. 10, 2015, pp. 671-677.
Japanese Office Action dated Aug. 9, 2022 in corresponding Japanese Patent Application No. 2021-111860 (with machine-generated English translation), 6 pages.
Japanese Office Action dated Nov. 15, 2022 in corresponding Japanese Patent Application No. 2021-111860 (with machine-generated English translation), 6 pages.

* cited by examiner

OPHTHALMOLOGIC INFORMATION PROCESSING APPARATUS, OPHTHALMOLOGIC SYSTEM, OPHTHALMOLOGIC INFORMATION PROCESSING METHOD, AND RECORDING MEDIUM

CROSS-REFERENCE TO RELATED APPLICATIONS

The present application is a continuation application of International Patent Application No. PCT/JP2018/038118, filed Oct. 12, 2018, which claims priority to Japanese Patent Application No. 2017-225876, filed Nov. 24, 2017. The contents of these applications are incorporated herein by reference in their entirety.

FIELD

The disclosure relates to an ophthalmologic information processing apparatus, an ophthalmologic system, an ophthalmologic information processing method, and a recording medium.

BACKGROUND

Age-related macular degeneration (AMD) is one of the causative diseases of visual disturbance. AMD is a disease in which a macular region is impaired directly or indirectly by aging. AMD is classified into exudative age-related macular degeneration (exudative AMD) and atrophic age-related macular degeneration (atrophic AMD). Exudative AMD is a disease in which a retina is damaged by invasion of choroidal neovascularization from the choroid to the lower layer of retinal pigment epithelium layer (hereinafter, RPE) or invasion of choroidal neovascularization between the retina and the RPE. Atrophic AMD is a disease in which the retina is damaged by gradual atrophy of the RPE and vision is gradually decreased.

Photo dynamic therapy (PDT), drug therapy, laser coagulation and the like are known as effective treatments of exudative AMD. On the other hand, effective treatment for atrophic AMD is not well established at present. Therefore, understanding the state of atrophic AMD is extremely important.

In atrophic AMD, so-called geographic atrophy (GA) is found in a predetermined region centered on a fovea. GA is specified from fundus images, fluorescein fluorescence fundus angiograms, fundus autofluorescnece inspection images, or the like, or GA is specified from tomographic images of the retina obtained using optical coherence tomography (for example, U.S. Unexamined Patent Application Publication No. 2015/0201829, Japanese Unexamined Patent Publication No. 2015-136626, Japanese Unexamined Patent Publication No. 2016-107148). The state of atrophic AMD can be understood by observing the specified GA (for example, Japanese Unexamined Patent Application Publication (Translation of PCT Application) No. 2014-505552).

SUMMARY

In order to understand the state of atrophic AMD (age-related macular degeneration), observing morphology (form) (shape, size) or distribution of the region (geographic atrophy region) with geographic atrophy is effective. However, in the conventional techniques, the morphology or the distribution of the geographic atrophy region could not be observed in detail. Thereby, it was difficult to make an accurate diagnosis of atrophic AMD.

According to some embodiments of the present invention, a new technique for observing morphology or distribution of an atrophy region in a fundus in detail can be provided.

One aspect of some embodiments is an ophthalmologic information processing apparatus, including: an analyzer configured to specify an atrophy region in a fundus by analyzing data of the fundus of a subject's eye acquired using optical coherence tomography; a storage unit storing image data of the fundus; and a display controller configured to cause a fundus image of the subject's eye to be displayed on a display means based on the image data stored in the storage unit, and to cause a region corresponding to the atrophy region in the fundus image to be displayed on the display means so as to be identifiable.

Another aspect of some embodiments is an ophthalmologic system, including: a data acquisition unit configured to acquire the data by scanning the subject's eye using optical coherence tomography; the display means; and the ophthalmologic information processing apparatus described above.

Further, another aspect of some embodiments is an ophthalmologic information processing method, including: an analysis step of specifying an atrophy region in a fundus by analyzing data of the fundus of a subject's eye acquired using optical coherence tomography; a display step of causing a fundus image of the subject's eye to be displayed on a display means based on the image data of the fundus, and of causing a region corresponding to the atrophy region in the fundus image to be displayed on the display means so as to be identifiable.

Further, another aspect of some embodiments is a non-transitory computer readable recording medium storing a program of causing a computer to execute each step of the ophthalmologic information processing method described above.

DETAILED DESCRIPTION

Figure 1:
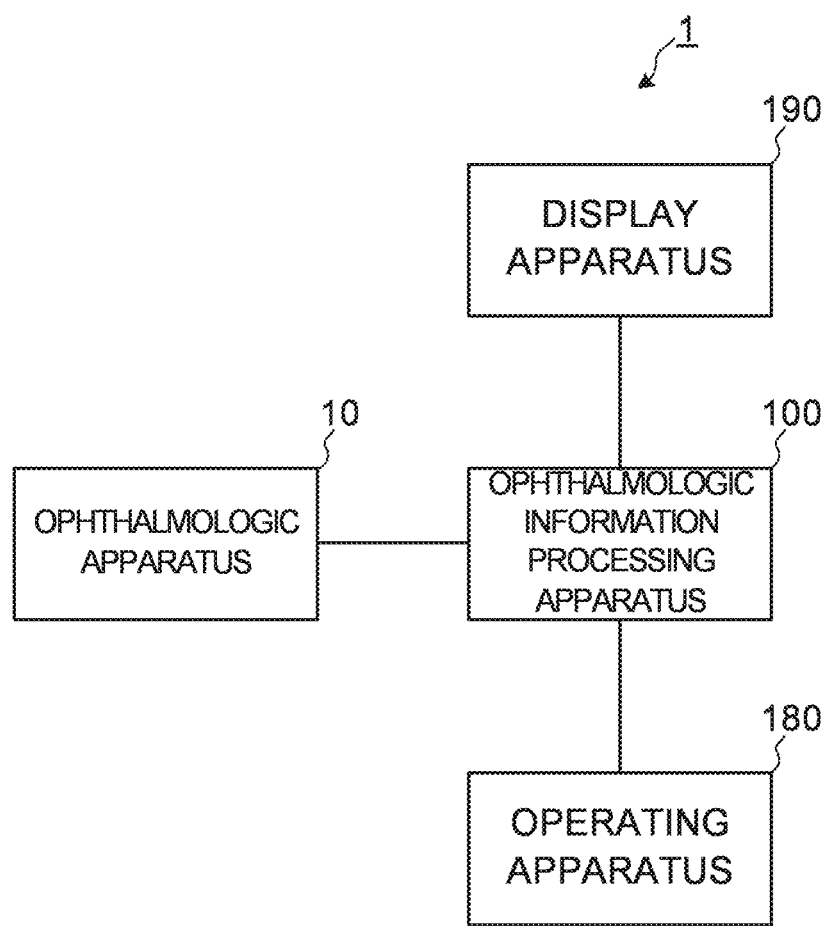
FIG. 1 is a schematic diagram illustrating an example of a configuration of an ophthalmologic system according to embodiments.

Referring now to the drawings, exemplary some embodiments of an ophthalmologic information processing apparatus, an ophthalmologic system, an ophthalmologic information processing method, a program, and a recording medium according to some embodiments of the present invention are described below. Any of the contents of the documents cited in the present specification and arbitrary known techniques may be applied to the embodiments below.

An ophthalmologic system according to the embodiments includes an ophthalmologic information processing apparatus. An ophthalmologic information processing method according to the embodiments is performed by the ophthalmologic information processing apparatus. The ophthalmologic information processing method according to the embodiments can be executed by a computer according to a program.

The ophthalmologic information processing apparatus according to the embodiments can perform predetermined analysis processing and predetermined display processing on data of a fundus of a subject's eye optically acquired using the ophthalmologic apparatus. The ophthalmologic apparatus according to some embodiments has the function of acquiring a front image of the fundus of the subject's eye. Examples of the ophthalmologic apparatus having the function of acquiring the front image of the fundus of the subject's eye include an optical coherence tomography (OCT, hereafter) apparatus, a fundus camera, a scanning laser ophthalmoscope (SLO), a slit lamp microscope, a surgical microscope, and the like. The ophthalmologic apparatus according to some embodiments has the function of measuring optical characteristics of the subject's eye. Examples of the ophthalmologic apparatus having the function of measuring optical characteristics of the subject's eye include a refractometer, a keratometer, a tonometer, a wave front analyzer, a specular microscope, a perimeter, and the like. The ophthalmologic apparatus according to some embodiments has the function of a laser treatment apparatus used for laser therapy.

[Ophthalmologic System]

FIG. 1 shows a block diagram of an example of the configuration of the ophthalmologic system according to the embodiments. The ophthalmologic system 1 according to the embodiments includes an ophthalmologic apparatus 10, an ophthalmologic information processing apparatus (ophthalmologic image processing apparatus, ophthalmologic analysis apparatus) 100, an operating apparatus 180, and a display apparatus 190.

The ophthalmologic apparatus 10 optically acquires data of the subject's eye. The ophthalmologic apparatus 10 optically acquires the data of the fundus of the subject's eye by scanning the fundus of the subject's eye. For example, the ophthalmologic apparatus 10 acquires three-dimensional OCT data of the fundus of the subject's eye using OCT. The ophthalmologic apparatus 10 can obtain an image of the fundus of the subject's eye from the acquired data of the subject's eye. The images of the fundus include a tomographic image of the fundus, and a front image of the fundus. Examples of the tomographic image of the fundus include a B scan image, and the like. Examples of the front image of the fundus include a C scan image, a shadowgram, a projection image, and the like. The ophthalmologic apparatus 10 sends the acquired data of the subject's eye to the ophthalmologic information processing apparatus 100.

In some embodiments, the ophthalmologic apparatus 10 and the ophthalmologic information processing apparatus 100 are connected via a data communication network. The ophthalmologic information processing apparatus 100 according to some embodiments receives data from one of a plurality of ophthalmologic apparatuses 10 selectively connected via the data communication network.

The ophthalmologic information processing apparatus 100 specifies a geographic atrophy region (atrophy region) by analyzing the acquired data of the subject's eye, and causes the geographic atrophy region in the front image or the tomographic image of the fundus to be displayed on the display apparatus 190 so as to be identifiable.

The ophthalmologic information processing apparatus 100 causes a region corresponding to the geographic atrophy region in the front image of the fundus formed from the acquired data of the subject's eye to be highlighted (displayed in highlighted manner). The ophthalmologic information processing apparatus 100 according to some embodiments forms the front image of the fundus from the acquired data of the subject's eye, performs position matching between the formed front image and the specified geographic atrophy region, and causes the front image of the fundus, on which the image representing the geographic atrophy region is overlaid, to be displayed, the image having been performed position matching.

The ophthalmologic information processing apparatus 100 causes the region corresponding to the geographic atrophy region in the tomographic image of the fundus formed from the acquired data of the subject's eye to be highlighted. The ophthalmologic information processing apparatus 100 according to some embodiments forms the tomographic image of the fundus from the acquired data of the subject's eye, performs position matching between the formed tomographic image and the specified geographic atrophy region, and causes the tomographic image of the fundus, on which the image representing the geographic atrophy region is overlaid, to be displayed, the image having been performed position matching.

The operating apparatus 180 and the display apparatus 190 provide the function for exchanging information between the ophthalmologic information processing apparatus 100 and the user, such as displaying information, inputting information, and inputting operation instructions, as a user interface unit. The operating apparatus 180 includes an operating device such as a lever, a button, a key, and pointing device. The operating apparatus 180 according to some embodiments includes a microphone for inputting information using sound. The display apparatus 190 includes a display device such as a flat-panel display. In some embodiments, the functions of the operating apparatus 180 and the display apparatus 190 are realized using a device in which a device having an input function such as a touch panel display and a device having a display function are integrated. In some embodiments, the operating apparatus 180 and the display apparatus 190 include a graphical user interface (GUI) for inputting and outputting information.

[Ophthalmologic Apparatus]

Figure 2:
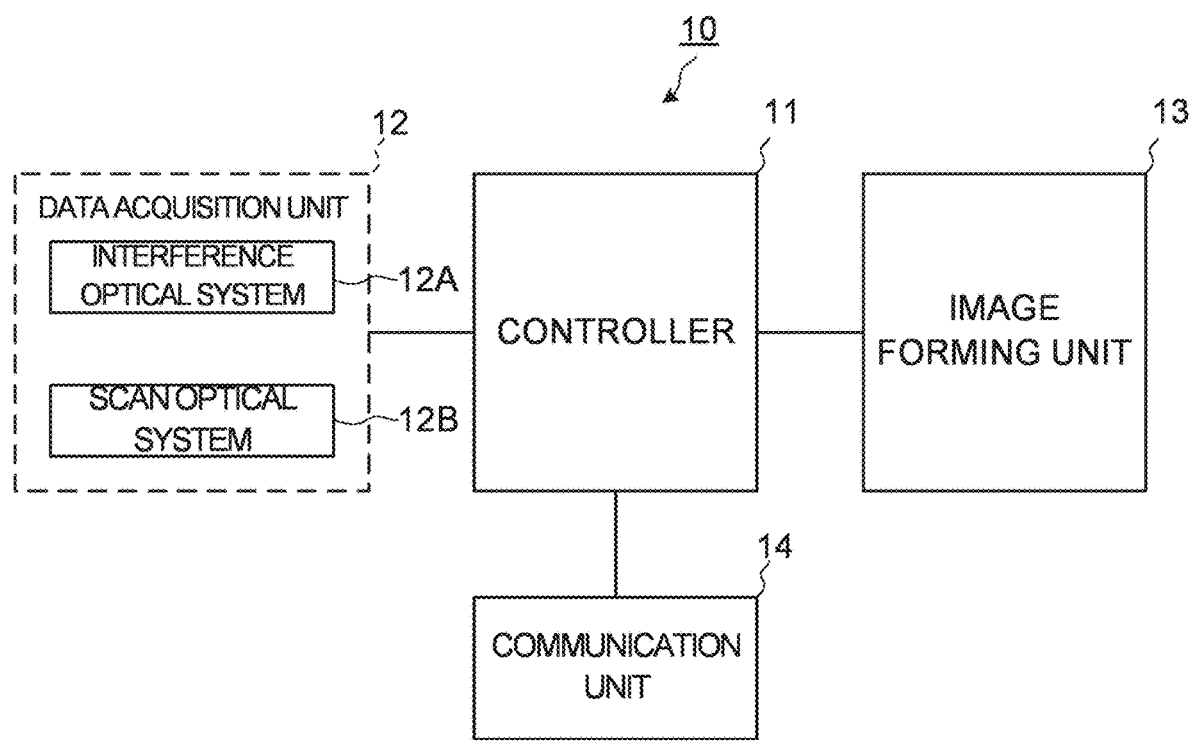
FIG. 2 is a schematic diagram illustrating an example of a configuration of an ophthalmologic apparatus according to the embodiments.

FIG. 2 shows a block diagram of an example of the configuration of the ophthalmologic apparatus 10 according to the embodiments.

The ophthalmologic apparatus 10 includes an optical system for acquiring OCT data of the subject's eye. The ophthalmologic apparatus 10 has a function of performing swept source OCT, but the embodiments are not limited to this. For example, the type of OCT is not limited to swept source OCT, and it may be the spectral domain OCT or the like. The swept source OCT is a technique that splits light from a wavelength sweep type (i.e., a wavelength scanning type) light source into measurement light and reference light; superposes the measurement light returning from the object to be measured with the reference light to generate interference light; detects the interference light with a balanced photodiode or the like; and applies the Fourier transform etc. to the detection data acquired through the tuning of wavelengths and the scanning of the measurement light to form an image. The spectral domain OCT is a technique that splits light from a low coherence light source into measurement light and reference light; superposes the measurement light returning from the object to be measured with the reference light to generate interference light; detects the spectral distribution of the interference light with a spectrometer; and applies the Fourier transform etc. to the detected spectral distribution to form an image.

The ophthalmologic apparatus 10 includes a controller 11, a data acquisition unit 12, an image forming unit 13, and a communication unit 14.

The controller 11 controls each part of the ophthalmologic apparatus 10. In particular, the controller 11 controls the data acquisition unit 12, the image forming unit 13, and the communication unit 14.

The data acquisition unit 12 acquires data (three-dimensional OCT data) of the subject's eye by scanning the subject's eye using OCT. The data acquisition unit 12 includes an interference optical system 12A and a scan optical system 12B.

The interference optical system 12A splits light from the light source (wavelength sweep type light source) into measurement light and reference light, makes returning light of the measurement light through the subject's eye and the reference light having traveled through a reference optical path interfere with each other to generate interference light, and detects the interference light. The interference optical system 12A includes at least a fiber coupler and a light receiver such as a balanced photodiode. The fiber coupler splits the light from the light source into the measurement light and the reference light, and makes returning light of the measurement light through the subject's eye and the reference light having traveled through a reference optical path interfere with each other to generate interference light. The light receiver detects the interference light generated by the fiber coupler. The interference optical system 12A may include the light source.

The scan optical system 12B changes an incident position of the measurement light on the fundus of the subject's eye by deflecting the measurement light generated by the interference optical system 12A, under the control of the controller 11. The scan optical system 12B includes, for example, an optical scanner disposed at a position optically conjugate with a pupil of the subject's eye. The optical scanner includes, for example, a galvano mirror that scans with the measurement light in the horizontal direction, a galvano mirror that scans with the measurement light in the vertical direction, and a mechanism that independently drives the galvano mirrors. With this, it is possible to scan the measurement light in an arbitrary direction in the fundus plane.

A detection result (detection signal) of the interference light obtained by the interference optical system 12A is an interference signal representing the spectrum of the interference light.

The image forming unit 13 forms image data of a tomographic image of the fundus of the subject's eye based on the data of the subject's eye acquired by the data acquisition unit 12, under the control of the controller 11. This processing includes noise removal (noise reduction), filtering, fast Fourier transform (FFT), and the like. The image data acquired in this manner is a data set including a group of image data formed by imaging the reflection intensity profiles of a plurality of A lines. Here, the A lines are the paths of the measurement light in the subject's eye. In order to improve the image quality, it is possible to repeatedly perform scan with the same pattern a plurality of times to collect a plurality of data sets, and to compose (i.e., average) the plurality of data sets.

The image forming unit 13 can form a B scan image, a C scan image, a projection image, a shadowgram, etc., by performing various renderings on the acquired three-dimensional OCT data. An image in an arbitrary cross section such as the B scan image or the C scan image is formed by selecting pixels (voxels) on a designated cross section from the three-dimensional OCT data. The projection image is formed by projecting the three-dimensional OCT data in a predetermined direction (Z direction, depth direction, A scan direction). The shadowgram is formed by projecting a part of the three-dimensional OCT data (for example, partial data corresponding to a specific layer) in a predetermined direction.

The ophthalmologic apparatus 10 according to some embodiments includes a data processor that performs various kinds of data processing (e.g., image processing) and various kinds of analysis processing on the image formed by the image forming unit 13. For example, the data processor performs various correction processes such as brightness correction and dispersion correction of images. The data processor can form volume data (voxel data) of the subject's eye by performing known image processing such as interpolation processing for interpolating pixels between tomographic images. In the case of displaying an image based on the volume data, the data processor performs rendering processing on the volume data so as to form a pseudo three-dimensional image viewed from a specific line-of-sight direction.

Each of the controller 11 and the image forming unit 13 includes a processor. The processor includes, for example, a circuit(s) such as, for example, a CPU (central processing unit), a GPU (graphics processing unit), an ASIC (application specific integrated circuit), and a PLD (programmable logic device). Examples of PLD include a simple programmable logic device (SPLD), a complex programmable logic device (CPLD), and a field programmable gate array (FPGA). The functions of the image forming unit 13 are realized by an image forming processor. In some embodiments, both of the functions of the controller 11 and the image forming unit 13 are realized by a single processor. In some embodiments, in case that the ophthalmologic apparatus 10 includes the data processor, the functions of the data processor are also realized by a processor.

The processor realizes, for example, the function according to the embodiments by reading out a computer program stored in a storage circuit or a storage device and executing the computer program. At least a part of the storage circuit or the storage apparatus may be included in the processor. Further, at least a part of the storage circuit or the storage apparatus may be provided outside of the processor.

The storage apparatus etc. stores various types of data. Examples of the data stored in the storage apparatus etc. include data (measurement data, photographic data, etc.) acquired by the data acquisition unit 12 and information related to the subject and the subject's eye. The storage apparatus etc. may store a variety of computer programs and data for the operation of each part of the ophthalmologic apparatus 10.

The communication unit 14 performs communication interface processing for sending or receiving information with the ophthalmologic information processing apparatus 100 under the control of the controller 11.

The ophthalmologic apparatus 10 according to some embodiments sends the image data of the subject's eye formed by the image forming unit 13 to the ophthalmologic information processing apparatus 100.

The ophthalmologic apparatus 10 according to some embodiments includes a fundus camera for acquiring an image of the fundus of the subject's eye, a scanning laser ophthalmoscope for acquiring an image of the fundus of the subject's eye, or a slit lamp microscope. In some embodiments, the fundus image acquired by the fundus camera is a fluorescein fluorescence fundus angiogram or a fundus autofluorescnece inspection image.

[Ophthalmologic Information Processing Apparatus]

Figure 3:
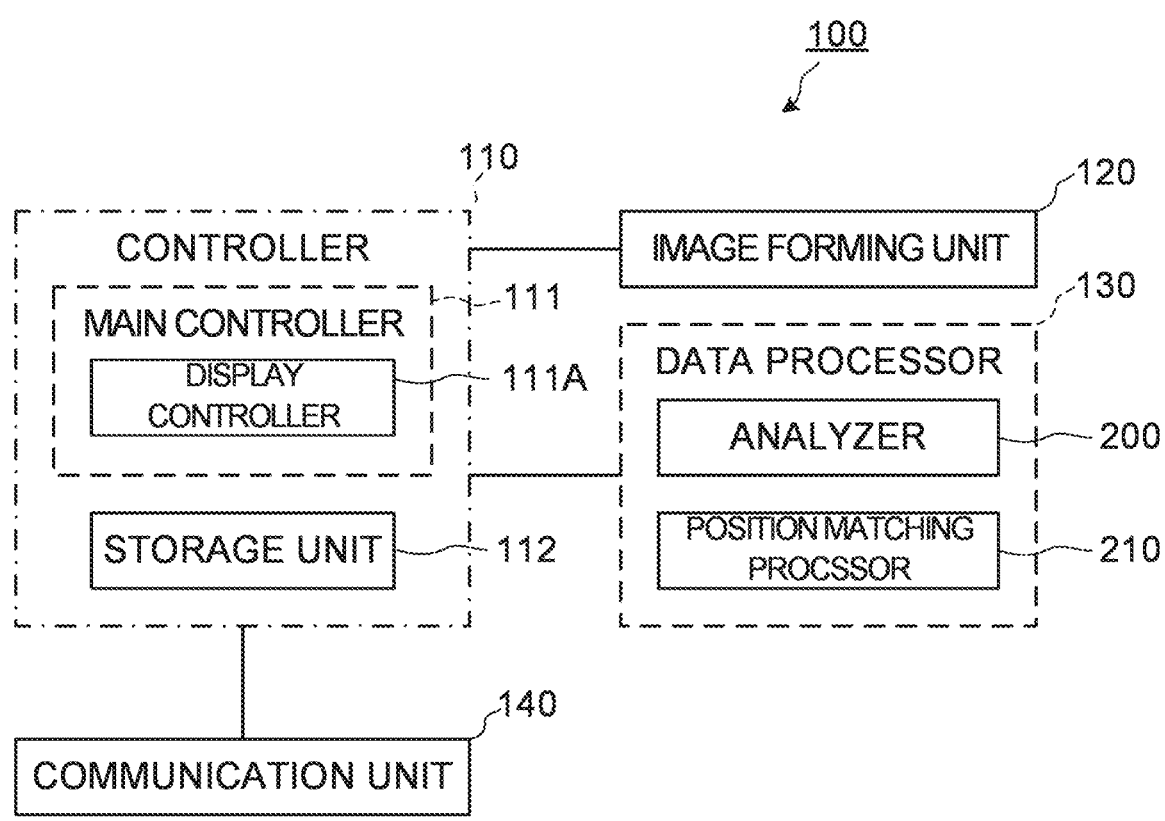
FIG. 3 is a schematic diagram illustrating an example of a configuration of an ophthalmologic information processing apparatus according to the embodiments.
Figure 4:
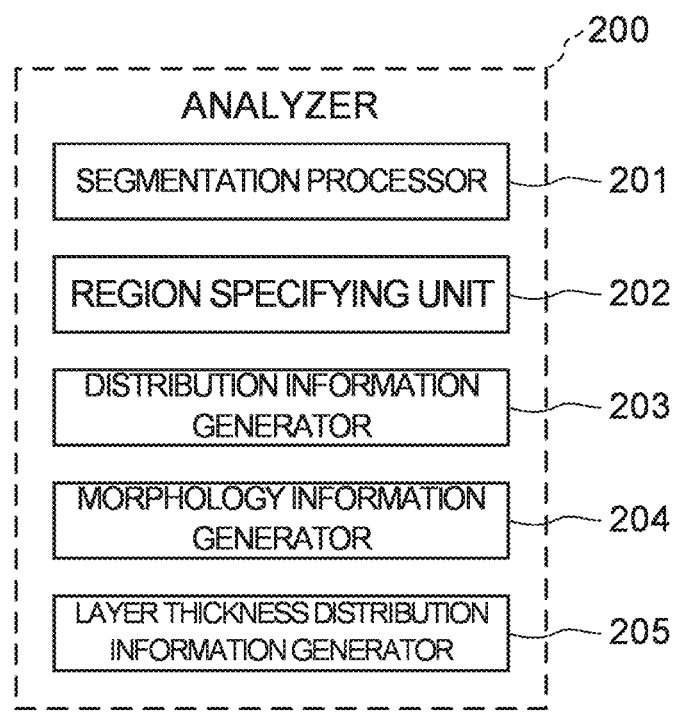
FIG. 4 is a schematic diagram illustrating an example of the configuration of the ophthalmologic information processing apparatus according to the embodiments.

FIGS. 3 and 4 show block diagrams of examples of the configuration of the ophthalmologic information processing apparatus 100 according to the embodiments. FIG. 3 shows a functional block diagram of the ophthalmologic information processing apparatus 100. FIG. 4 shows a functional block diagram of an analyzer 200 of FIG. 3.

The ophthalmologic information processing apparatus 100 according to the embodiments analyzes the data of the fundus of the subject's eye acquired by the ophthalmologic apparatus 10 to specify a geographic atrophy region in the fundus. The ophthalmologic information processing apparatus 100 causes the specified geographic atrophy region in the front image or the tomographic image of the fundus to be displayed on the display apparatus 190 so as to be identifiable.

The ophthalmologic information processing apparatus 100 includes a controller 110, an image forming unit 120, a data processor 130, and a communication unit 140.

The image forming unit 120 forms a B scan image, a C scan image, a projection image, a shadowgram, or the like from the three-dimensional OCT data acquired by the ophthalmologic apparatus 10 under the control of the controller 110. The image forming unit 120 can form the above image in the same manner as the image forming unit 13.

The data processor 130 performs various kinds of data processing (e.g., image processing) and various kinds of analysis processing on an image formed by the image forming unit 120. For example, the data processor 130 performs various correction processes such as brightness correction and dispersion correction of images. The data processor 130 can form volume data (voxel data) of the subject's eye by performing known image processing such as interpolation processing for interpolating pixels between tomographic images. In the case of displaying an image based on the volume data, the data processor 130 performs rendering processing on the volume data so as to form a pseudo three-dimensional image viewed from a specific line-of-sight direction.

The data processor 130 performs predetermined data processing on the formed image of the subject's eye. The processing unit 130 includes the analyzer 200 and a position matching processor 210.

The analyzer 200 performs predetermined analysis processing on the image data of the fundus of the subject's eye formed by the image forming unit 120 (or the image data of the fundus of the subject's eye acquired by the ophthalmologic apparatus 10). Examples of the analysis processing according to some embodiments include specifying processing of the geographic atrophy region in the fundus, generating processing of the distribution information of the geographic atrophy region, generating processing of the morphology information of the geographic atrophy region, generating processing of the distribution information of layer thickness in the fundus, and the like.

The analyzer 200 include a segmentation processor 201, a region specifying unit 202, a distribution information generator 203, a morphology information generator 204, and a layer thickness distribution information generator 205.

The segmentation processor 201 specifies a plurality of layer regions in the A scan direction based on the data of the subject's eye acquired by the ophthalmologic apparatus 10. The segmentation processor 201 according to some embodiments analyzes the three-dimensional OCT data to specify a plurality of partial data sets corresponding to a plurality of tissues of the subject's eye. The segmentation processing is image processing for specifying specific tissues and/or tissue boundaries. For example, the segmentation processor 201 obtains the gradients of the pixel values (i.e., brightness values) in each A scan image included in the OCT data, and specifies a position where the gradient value is large to be a tissue boundary. Note that the A scan image is one-dimensional image data extending in the depth direction of the fundus. The depth direction of the fundus is defined as, for example, the Z direction, the incident direction of the OCT measurement light, the axial direction, the optical axis direction of the interference optical system, or the like.

In a typical example, the segmentation processor 201 specifies a plurality of partial data sets corresponding to a plurality of layer tissues of the fundus by analyzing the three-dimensional OCT data representing the fundus (the retina, the choroid, etc.) and the vitreous body. Each partial data set is defined by the boundaries of the layer tissue.

Examples of the layer tissue specified as the partial data set include a layer tissue constituting the retina. Examples of the layer tissue constituting the retina include the inner limiting membrane, the nerve fiber layer, the ganglion cell layer, the inner plexiform layer, the inner nuclear layer, the outer plexiform layer, the outer nuclear layer, the external limiting membrane, the photoreceptor layer, the retinal pigment epithelium layer, and the like. The segmentation processor 201 can specify a partial data set corresponding to the Bruch membrane, the choroid, the sclera, the vitreous body, or the like. The segmentation processor 201 according to some embodiments specifies a partial data set corresponding to the site of lesion. Examples of the site of lesion include a detachment part, an edema, a bleeding site, a tumor, a drusen, and the like.

The segmentation processor 201 according to some embodiments specifies, as the Bruch membrane, a layer tissue for a predetermined number of pixels on the sclera side with respect to the RPE, and acquires, as the partial data set of the Bruch membrane, the partial data set corresponding to the layer tissue.

The region specifying unit 202 specifies a region corresponding to two layer tissues for specifying the geographic atrophy region by analyzing a plurality of partial data sets of the layer tissues specified by the segmentation processor 201. The region specifying unit 202 according to some embodiments specifies a first region and a second region, the first region corresponding to a layer tissue on the sclera side with respect to a region corresponding to the Bruch membrane, the second region corresponding to a layer region from a region corresponding to the inner limiting membrane to a region corresponding to the RPE. In some embodiments, the second region is a region corresponding to a layer tissue on the cornea side from the region corresponding to the Bruch membrane.

The distribution information generator 203 obtains a contrast ratio for each A scan based on the pixel values in the first region and the second region which are specified by the region specifying unit 202, and generates two-dimensional distribution information of the contrast ratio in the fundus plane (plane orthogonal to the A scan direction). In some embodiments, the distribution information generator 203 generates the distribution information of the ratio of the integrated value of the pixel values of the first region specified by the region specifying unit 202 and the integrated value of the pixel values of the second region specified by the layer region specifying unit 202, for each A scan. The distribution information generator 203 according to some embodiments obtains, as the contrast ratio, the ratio of the integrated value of the pixel values in the A scan direction of the second region to the integrated value of the pixel values in the A scan direction of the first region, and generates the two-dimensional distribution information of the obtained contrast ratio. The two-dimensional distribution information of the contrast ratio is hereinafter referred to as a contrast map.

The analyzer 200 specifies a position where the contrast ratio is large, as a position where signal components are attenuated due to the geographic atrophy, in the contrast map generated by the distribution information generator 203. The analyzer 200 specifies the geographic atrophy region based on the specified position. For example, the analyzer 200 specifies, as the geographic atrophy region, a region including positions where the contrast ratio is equal to or larger than a predetermined threshold value, in the contrast map generated by the distribution information generator 203. Techniques related to such a method for specifying a geographic atrophy region are disclosed in U.S. Unexamined Patent application Publication No. 2015/0201829, Japanese Unexamined Patent Application Publication No. 2015-136626, or Japanese Unexamined Patent Application Publication No. 2016-107148.

The morphology information generator 204 generates morphology information representing morphology of the specified geographic atrophy region. Examples of the morphology information include the area of the geographic atrophy region(s), the outer perimeter of the geographic atrophy region(s), and the like. The morphology information generator 204 can obtain the area of the geographic atrophy region(s) or the outer perimeter of the geographic atrophy region(s) by applying a known method to the image in which the geographic atrophy region(s) is(are) depicted. The morphology information generator 204 according to some embodiments generates the morphology information for each of the specified geographic atrophy regions. The morphology information generator 204 according to some embodiments generates, as the morphology information, the total value of morphological parameters (areas, outer perimeters) for each of the specified geographic atrophy regions. In some embodiments, the morphology information includes the number of the specified geographic atrophy regions.

The layer thickness distribution information generator 205 specifies a thickness in the A scan direction of each of the layer tissues by analyzing the partial data sets of the plurality of the layer tissues specified by the segmentation processor 201, and generates the two-dimensional distribution information of the layer thickness of the each layer in the fundus plane. The layer thickness distribution information generator 205 according to some embodiments generates the two-dimensional distribution information (distribution information of the plane orthogonal to the A scan direction) of the layer thickness of the one or more layer tissues designated using the operating apparatus 180. The layer thickness distribution information generator 205 according to some embodiments generates the two-dimensional distribution information of the layer thickness of at least one of the inner limiting membrane, the nerve fiber layer (NFL), the ganglion cell layer (GCL), the inner plexiform layer (IPL), the inner nuclear layer (INL), the outer plexiform layer (OPL), the outer nuclear layer (ONL), the external limiting membrane (ELM), the retinal pigment epithelium layer (RPE), the choroid, the sclera, and the choroidal-scleral interface (CSI), or two or more adjacent layers.

The position matching processor 210 performs position matching (registration) between a front image of the fundus formed by the image forming unit 120 and an image representing the geographic atrophy region specified by the analyzer 200. The position matching processor 210 performs position matching between the tomographic image of the fundus formed by the image forming unit 120 and the image representing the geographic atrophy region specified by the analyzer 200. The position matching processor 210 can perform position matching using known processing such as affine transformation for performing enlargement, reduction, rotation, or the like of the image.

The position matching processing includes, for example, processing for detecting characteristic sites from the both images and processing for performing position matching of the both images on the base of the both characteristic sites. In some embodiments, the position matching processing includes processing for specifying a position in the image representing the geographic atrophy region in the front image or the tomographic image using position information of the geographic atrophy region in the front image or the tomographic image of the fundus and processing for performing position matching of the image representing the specified geographic atrophy region with respect to the front image or the tomographic image.

The position matching processor 210 performs position matching between the tomographic image of the fundus formed by the image forming unit 120 and the image representing the geographic atrophy region specified by the analyzer 200.

The communication unit 140 performs communication interface processing for sending or receiving information with the communication unit 14 of the ophthalmologic information processing apparatus 100 under the control of the controller 110.

The controller 110 controls each part of the ophthalmologic information processing apparatus 100. In particular, the controller 110 controls the image forming unit 120, the data processor 130, and the communication unit 140. The controller 110 includes the main controller 111 and a storage unit 112. The main controller 111 includes the display controller 111A.

The display controller 111A causes the various information to be displayed on the display apparatus 190. For example, the display controller 111A causes the fundus image (front image, tomographic image) of the subject's eye formed by the image forming unit 120 or the image of the data processing result obtained by the data processor 130 to be displayed on the display apparatus 190. In particular, the display controller 111A causes the fundus image of the subject's eye to be displayed on the display apparatus 190, and causes the region corresponding to the geographic atrophy region in the fundus image to be displayed on the display apparatus 190 so as to be identifiable. The display controller 111A according to some embodiments causes the fundus image of the subject's eye to be displayed on the display apparatus 190, and causes the region corresponding to the geographic atrophy region in the fundus image to be highlighted on the display apparatus 190. For example, the display controller 111A controls the display apparatus 190 to display the geographic atrophy region or its background region such that the brightness of the pixels in the geographic atrophy region or its background region is higher than the brightness of the pixels in the other regions. The display controller 111A according to some embodiments causes an image in which the image representing the geographic atrophy region performed position matching by the position matching processor 210 is overlaid on the fundus image to be displayed on the display apparatus 190.

Further, the display controller 111A causes the morphology information generated by the morphology information generator 204 to be displayed on the display apparatus 190. The display controller 111A according to some embodiments causes the morphology information generated by the morphology information generator 204 to be displayed on the display apparatus 190 in association with the geographic atrophy region corresponding to the morphology information.

The controller 110 controls each part of the ophthalmologic system 1 based on operation instruction signal corresponding to the operation content of the user on the operating apparatus 180.

Each of the controller 110, the image forming unit 120, and the data processor 130 includes a processor. The functions of the image forming unit 120 is realized by an image forming processor. The functions of the data processor 130 is realized by a data processing processor. In some embodiments, at least two functions of the controller 110, the image forming unit 120, and the data processor 130 are realized by a single processor.

The storage unit 112 stores various kinds of data. Examples of the data stored in the storage unit 112 include data (measurement data, photographic data, etc.) acquired by the ophthalmologic apparatus 10, image data formed by the image forming unit 120, data processing result(s) obtained by the data processor 130, information related to the subject and the subject's eye, and the like. The storage unit 112 may store a variety of computer programs and data for the operation of each part of the ophthalmologic information processing apparatus 100.

The display apparatus 190 is an example of the "display means" according to the embodiments. The geographic atrophy region is an example of the "atrophy region" according to the embodiments.

Operation Example

Examples of the operation of the ophthalmologic information processing apparatus 100 according to some embodiments will be described.

Figure 5:
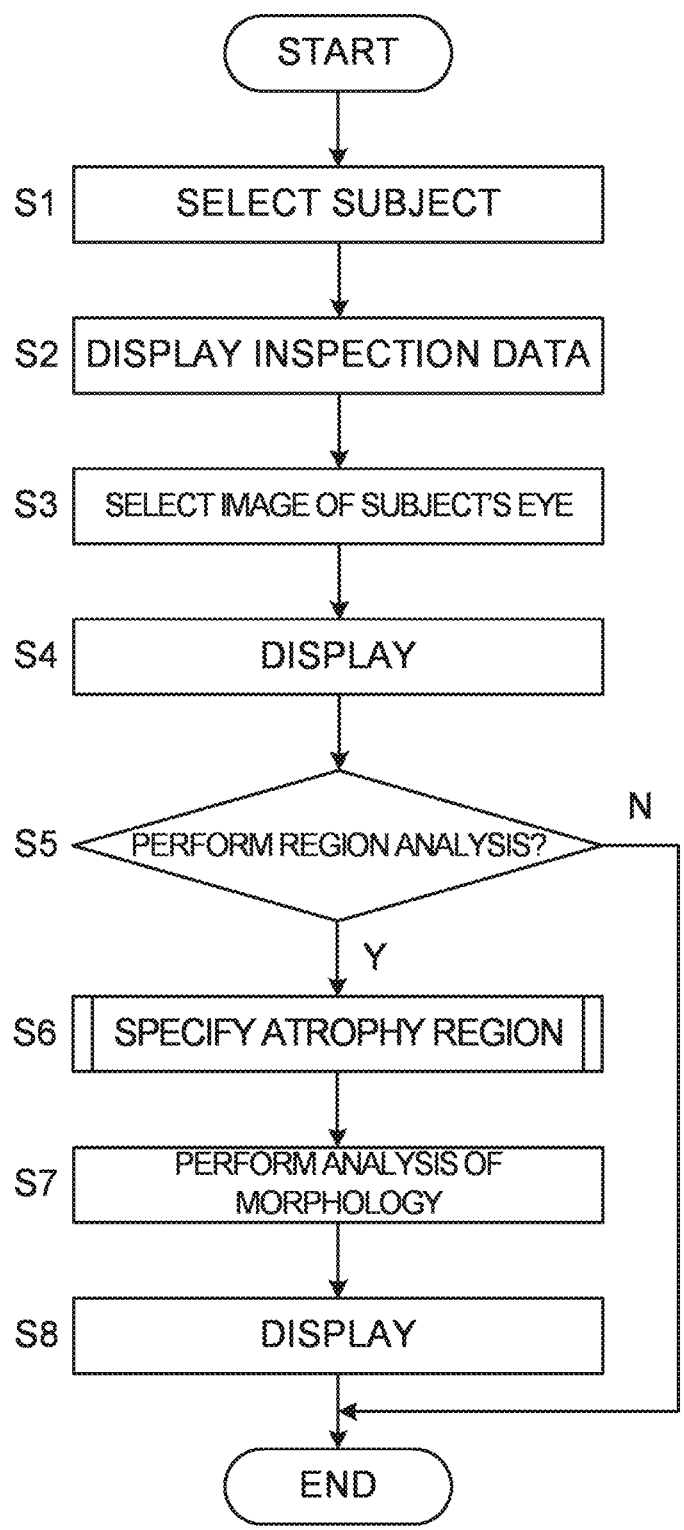
FIG. 5 is a schematic diagram illustrating an example of an operation flow of the ophthalmologic information processing apparatus according to the embodiments.

FIG. 5 shows an example of the operation of the ophthalmologic information processing apparatus 100 according to the embodiments. FIG. 5 shows a flowchart of an example of the operation of the ophthalmologic information processing apparatus 100. In FIG. 5, it is assumed that the three-dimensional OCT data of the subject's eye acquired by the ophthalmologic apparatus 10 has already stored in the ophthalmologic information processing apparatus 100 (storage unit 112).

(S1: Select Subject)

The user selects a subject by inputting the subject ID using the operating apparatus 180.

(S2: Display Inspection Data)

The storage unit 112 stores a database in which the inspection data of the subject is associated in advance corresponding to the subject ID. The controller 110 searches the database using the subject ID input in step S1 as a search key, and acquires the inspection data corresponding to the subject ID. The display controller 111A causes the inspection data corresponding to the subject ID acquired by searching the database to be displayed on the display apparatus 190. The inspection data includes one or more fundus images of the subject's eye acquired in the past inspection.

(S3: Select Image of Subject's Eye)

The ophthalmologic information processing apparatus 100 causes the user to select the image of the subject's eye to be analyzed among the one or more images of the subject's eye in the inspection data of the subject displayed on the display apparatus 190 in step S2. The subject operates the operating apparatus 180 to select the image of the subject's eye to be analyzed. The controller 110 receives the operation instruction signal corresponding to the operation content of the operating apparatus 180 by the user.

(S4: Display)

The display controller 111A selects the image of the subject's eye designated based on the operation instruction signal input in step S3 to cause the selected image of the subject's eye to be displayed on the display apparatus 190.

(S5: Perform Region Analysis?)

Next, the controller 110 determines whether or not to perform analysis of the geographic atrophy region for the image of the subject's eye displayed in step S4. The controller 110 can determine whether or not to perform analysis of the geographic atrophy region based on the operation instruction signal corresponding to the operation content to instruct analysis execution on the operating apparatus 180.

When it is determined that the analysis of the geographic atrophy region is to be performed (S5: Y), the operation of the ophthalmologic information processing apparatus 100 proceeds to step S6. When it is determined that the analysis of the geographic atrophy region analysis is not to be performed (S5: N), the ophthalmologic information processing apparatus 100 terminates the operation (END).

(S6: Specify Atrophy Region)

When it is determined that the analysis of the geographic atrophy region is to be performed in step S5 (S5: Y), the controller 110 controls the analyzer 200 to specify the geographic atrophy region by performing analysis of the geographic atrophy region. Details of step S6 will be described later. The controller 110 stores region specification information for specifying a position or a shape of the geographic atrophy region on the fundus in the storage unit 112 in association with the subject or the subject's eye.

(S7: Perform Analysis of Morphology)

Subsequently, the controller 110 controls the morphology information generator 204 to calculate an area and an outer perimeter of each of the geographic atrophy regions specified in step S6. The morphology information generator 204 generates the morphology information including the total value of the areas of the geographic atrophy regions, the total value of the outer perimeters of the geographic atrophy regions, and the number of the specified geographic atrophy regions. The controller 110 stores the morphology information generated in step S7 along with the above region specification information in the storage unit 112 in association with the subject or the subject's eye.

The controller 110 according to some embodiments controls the layer thickness distribution information generator 205 to generate the two-dimensional distribution information of the layer thickness of each layer in the fundus. The controller 110 stores the distribution information generated in step S7 along with the above region specification information in the storage unit 112 in association with the subject or the subject's eye.

(S8: Display)

Next, the controller 110 controls the position matching processor 210 to perform position matching between the front image of the fundus formed by the image forming unit 120 in advance and the image representing the geographic atrophy region specified in step S6. The display controller 111A causes the image representing the geographic atrophy region superimposed on the front image of the fundus to be displayed on the display apparatus 190. Here, the front image of the fundus may be a shadowgram ranging from RPE to the Bruch membrane. Further, the display controller 111A causes the morphology information generated in step S7 to be displayed on the display apparatus 190 in association with the geographic atrophy region corresponding to the morphology information.

In the same manner, the controller 110 controls the position matching processor 210 to perform position matching between the tomographic image of the fundus formed by the image forming unit 120 in advance and the image representing the geographic atrophy region specified in step S6. The display controller 111A causes the image representing the geographic atrophy region superimposed on the tomographic image of the fundus to be displayed on the display apparatus 190. Further, the display controller 111A causes the morphology information generated in step S7 to be displayed on the display apparatus 190 in association with the geographic atrophy region corresponding to the morphology information. This terminates the operation of the ophthalmologic information processing apparatus 100 (END).

Next, an example of the operation of step S6 in FIG. 5 will be described while referring to FIGS. 6 to 12.

Figure 6:
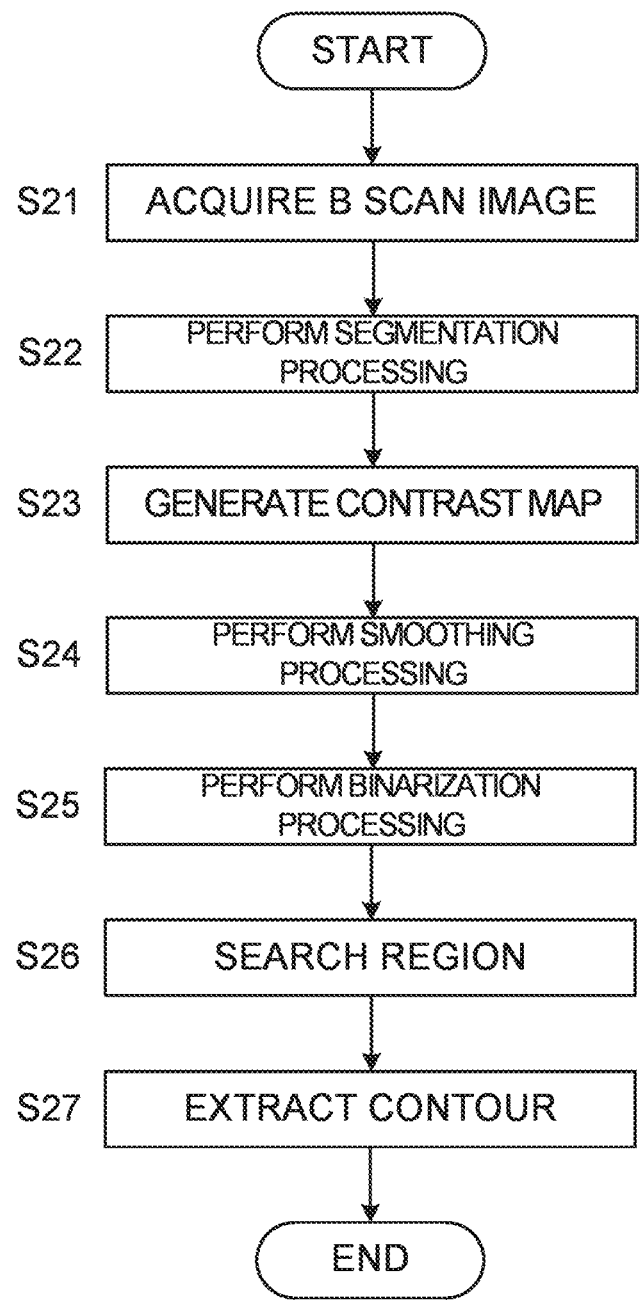
FIG. 6 is a schematic diagram illustrating an example of an operation flow of the ophthalmologic information processing apparatus according to the embodiments.
Figure 7:
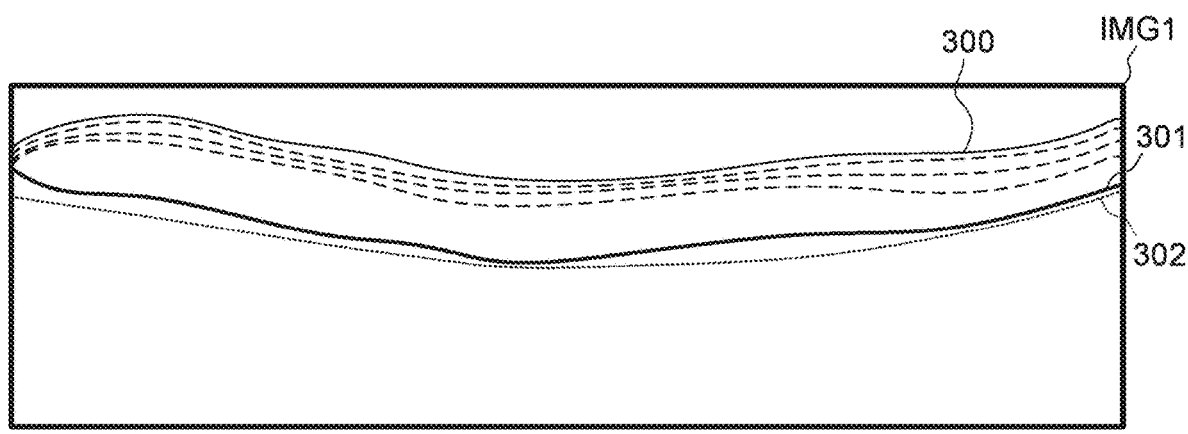
FIG. 7 is a schematic diagram for explaining an operation of the ophthalmologic information processing apparatus according to the embodiments.
Figure 8:
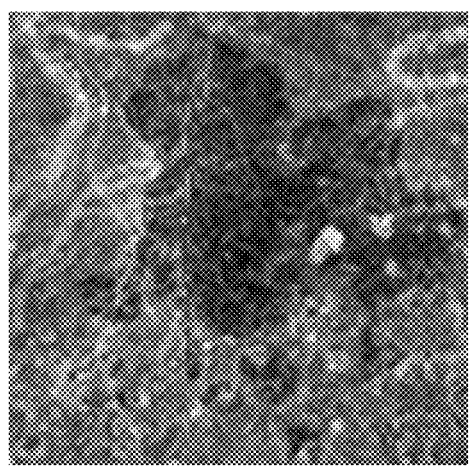
FIG. 8 is a schematic diagram for explaining an operation of the ophthalmologic information processing apparatus according to the embodiments.
Figure 9A:
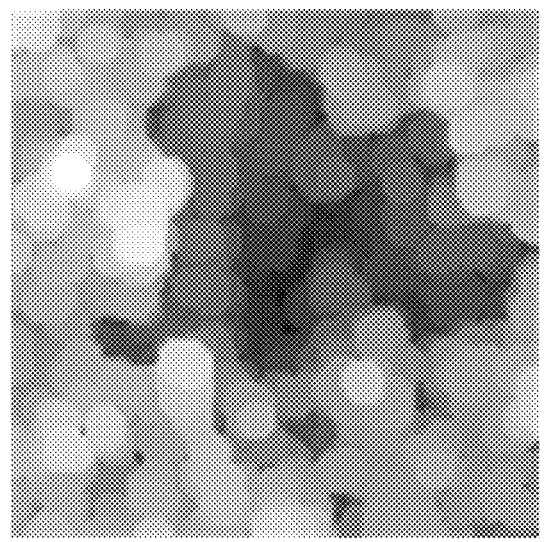
FIG. 9A is a schematic diagram for explaining an operation of the ophthalmologic information processing apparatus according to the embodiments.
Figure 9B:
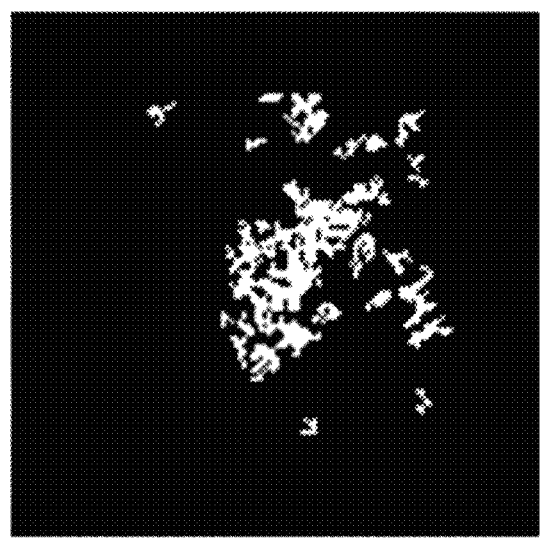
FIG. 9B is a schematic diagram for explaining an operation of the ophthalmologic information processing apparatus according to the embodiments.
Figure 10:
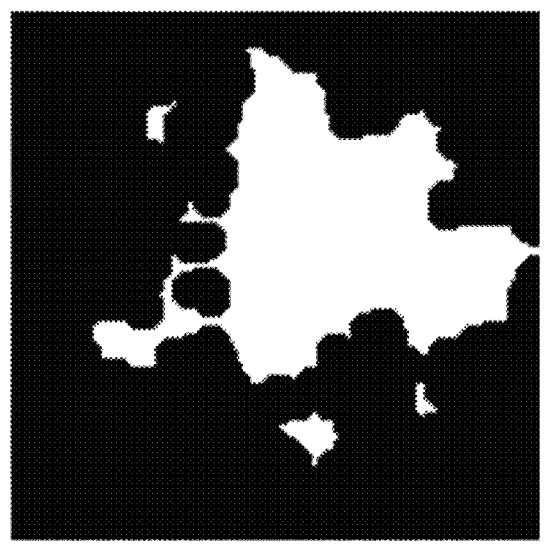
FIG. 10 is a schematic diagram for explaining an operation of the ophthalmologic information processing apparatus according to the embodiments.
Figure 11:
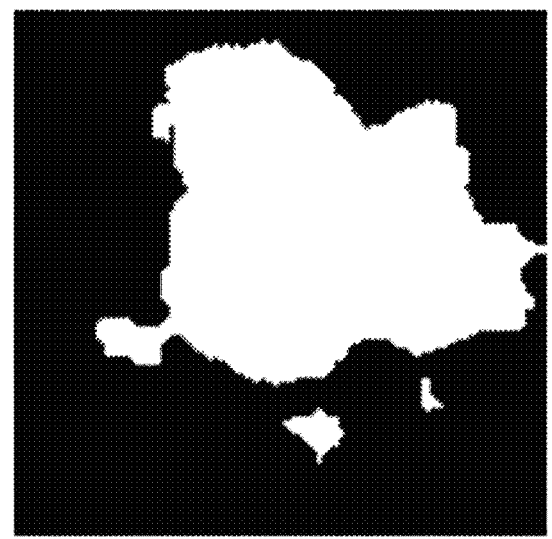
FIG. 11 is a schematic diagram for explaining an operation of the ophthalmologic information processing apparatus according to the embodiments.
Figure 12:
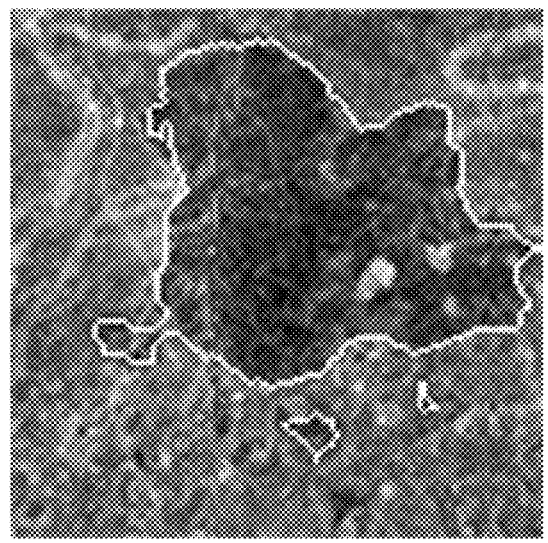
FIG. 12 is a schematic diagram for explaining an operation of the ophthalmologic information processing apparatus according to the embodiments.

FIG. 6 shows a flow of an example of the operation of step S6 in FIG. 5. FIG. 7 is an operation explanatory diagram for step S22. FIG. 8 is an operation explanatory diagram for step S23. FIG. 9A is an operation explanatory diagram for step S24. FIG. 9B is an operation explanatory diagram for step S25. FIG. 10 is an operation explanatory diagram for step S26. FIGS. 11 and 12 are operation explanatory diagrams for step S27.

(S21: Acquire B Scan Image)

When it is determined that the analysis of the geographic atrophy region is to be performed (S5: Y), the controller 110 reads out the data of the fundus of the subject's eye stored in the storage unit 112, and controls the image forming unit 120 to form a B scan image based on the read data. In some embodiments, in step S21, the B scan image is acquired from the ophthalmologic apparatus 10.

(S22: Perform Segmentation Processing)

The controller 110 controls the segmentation processor 201 to perform segmentation processing on the B scan image acquired in step S21. The segmentation processor 201 specifies a plurality of layer regions in the A scan direction for the B scan image acquired in step S21. As shown in FIG. 7, the segmentation processor 201 specifies the inner limiting membrane 300, the nerve fiber layer, the ganglion cell layer, the inner plexiform layer, the inner nuclear layer, the outer plexiform layer, the outer nuclear layer, the external limiting membrane, the photoreceptor layer, the RPE 301 which constitute the retina, in the B scan image IMG1. Further, the segmentation processor 201 specifies, as the Bruch membrane 302, a layer tissue for a predetermined number of pixels on the sclera side with respect to the specified RPE 301.

(S23: Generate Contrast Map)

Subsequently, the controller 110 controls the data processor 130 to generate the contrast map using the result of the segmentation processing in step S22. That is, the region specifying unit 202 specifies the first region and the second region by analyzing the partial data sets of the plurality of layer regions specified by the segmentation processor 201. The first region corresponds to the layer tissues on the sclera side from the region corresponding to the Bruch membrane 302. The second region corresponds to the layer tissues from the region corresponding to the inner limiting membrane 300 to the region corresponding to the RPE 301.

The distribution information generator 203 obtains, as the contrast ratio, the ratio of the integrated value of the pixel values in the A scan direction of the second region to the integrated value of the pixel values in the A scan direction of the first region, and generates the two-dimensional distribution information of the obtained contrast ratio (FIG. 8).

(S24: Perform Smoothing Processing)

Next, the controller 110 controls the data processor 130 to perform smoothing processing on the contrast map generated in step S23. Focusing on the fact that the change in pixel value between adjacent pixels generally tends to be small and that the noise component superimposed on the pixel value is also similar, the contrast map from which the noise component is removed by performing smoothing processing can be obtained (FIG. 9A).

(S25: Perform Binarization Processing)

Subsequently, the controller 110 controls the data processor 130 to perform binarization processing on the contrast map after the smoothing processing in step S24. Thereby, a binarized map as shown in FIG. 9B is obtained.

(S26: Search Region)

The controller 110 controls the analyzer 200 to search a region by applying a known region expansion method to the binarized map obtained in step S25 (FIG. 10).

(S27: Extract Contour)

The controller 110 controls the analyzer 200 to extract the contour of the region by performing known contour extraction processing on the region obtained by searching in step S26 (FIG. 11). The analyzer 200 specifies the geographic atrophy region based on the extracted contour (FIG. 12). This terminates the processing of step S6 in FIG. 5 (END).

Figure 13:
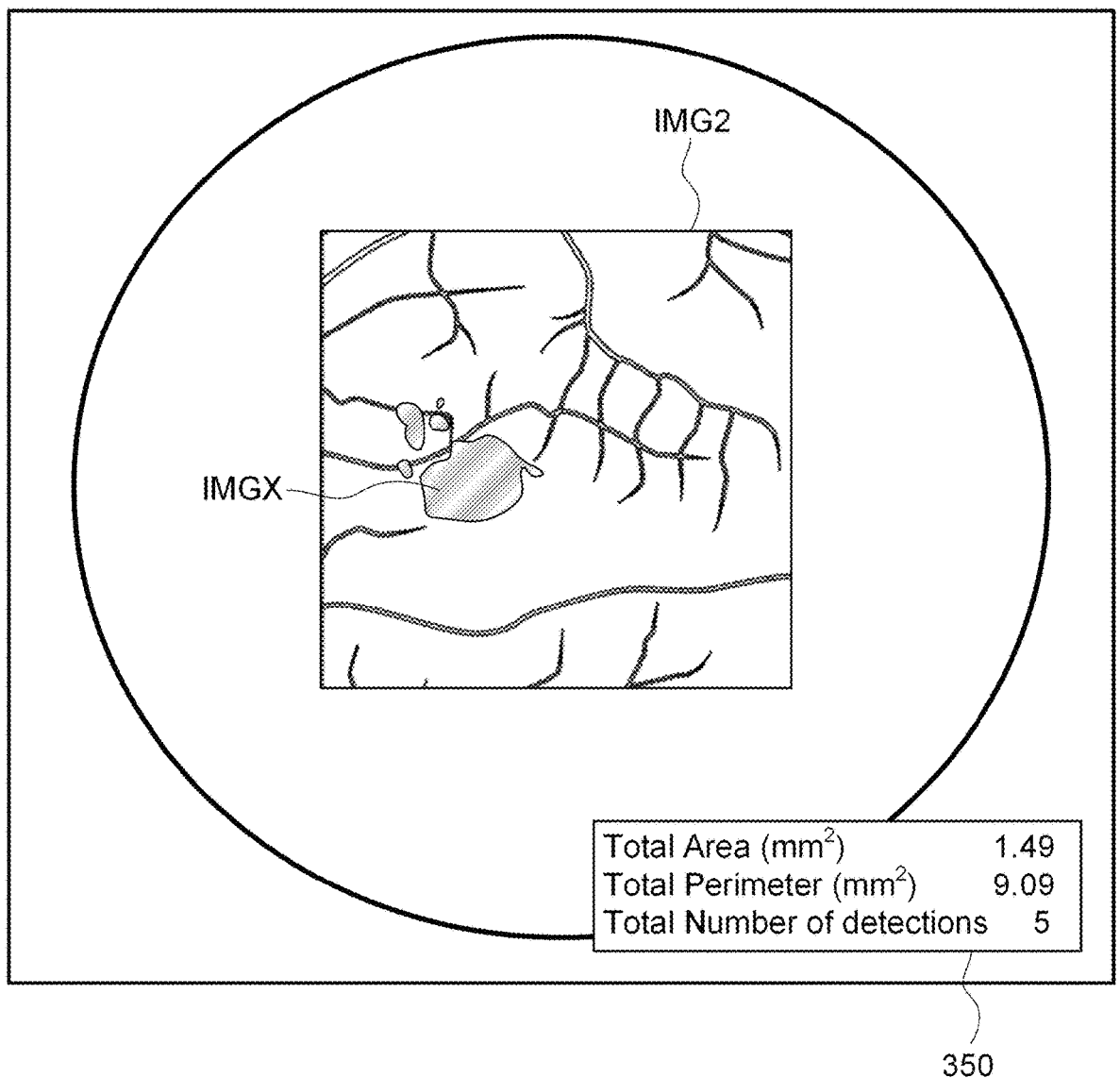
FIG. 13 is a schematic diagram for explaining an operation of the ophthalmologic information processing apparatus according to the embodiments.

FIG. 13 shows an example of the analysis information displayed on the display apparatus 190 in some embodiments.

For example, in step S8, the display controller 111A causes the image IMGX representing the geographic atrophy region superimposed on the shadowgram (the front image of the fundus) IMG2 to be displayed on the display apparatus 190.

Further, the display controller 111A can cause the morphology information 350 including the total value of the area(s) of the geographic atrophy region(s), the total value of the outer perimeter(s) of the geographic atrophy region(s), and the number of the geographic atrophy region(s) to be displayed on the display apparatus 190. The display controller 111A according to some embodiments causes the morphology information of each of the geographic atrophy regions to be displayed on the display apparatus 190 in association with the geographic atrophy region corresponding to the morphology information. Thereby, the morphology of each of the geographic atrophy regions can be observed in detail.

Figure 14:
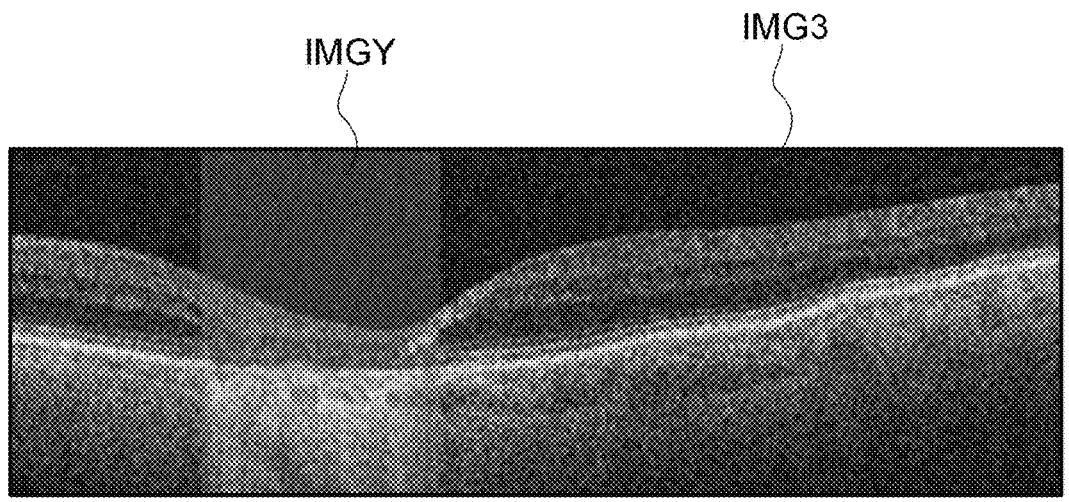
FIG. 14 is a schematic diagram for explaining an operation of the ophthalmologic information processing apparatus according to the embodiments.

FIG. 14 shows another example of the analysis information displayed on the display apparatus 190 in some embodiments.

For example, in step S8, the display controller 111A causes the image IMGY (image of B scan cross section) representing the geographic atrophy region superimposed on the B scan image IMG3 of the fundus to be displayed on the display apparatus 190. Thereby, the morphology of the geographic atrophy region can be observed in the B scan image in detail.

Modification Example

The configuration according to some embodiments is not limited to the above configuration.

First Modification Example

The relative position of the geographic atrophy region with respect to the macular region (fovea) is effective for the diagnosis of atrophic AMD. The ophthalmologic information processing apparatus according to a modification example of some embodiments analyzes the data of the fundus of the subject's eye acquired by the ophthalmologic apparatus to generate position information representing a position or a distance of the geographic atrophy region with respect to the macular region (fovea) on the fundus.

In the following, the ophthalmologic information processing apparatus according to the modification example of the embodiments will be described focusing on differences from the ophthalmologic information processing apparatus according to the above embodiments. The difference between the configuration of the ophthalmologic informa-tion processing apparatus according to the present modification example and the configuration of the ophthalmologic information processing apparatus 100 described above is the analyzer.

Figure 15:
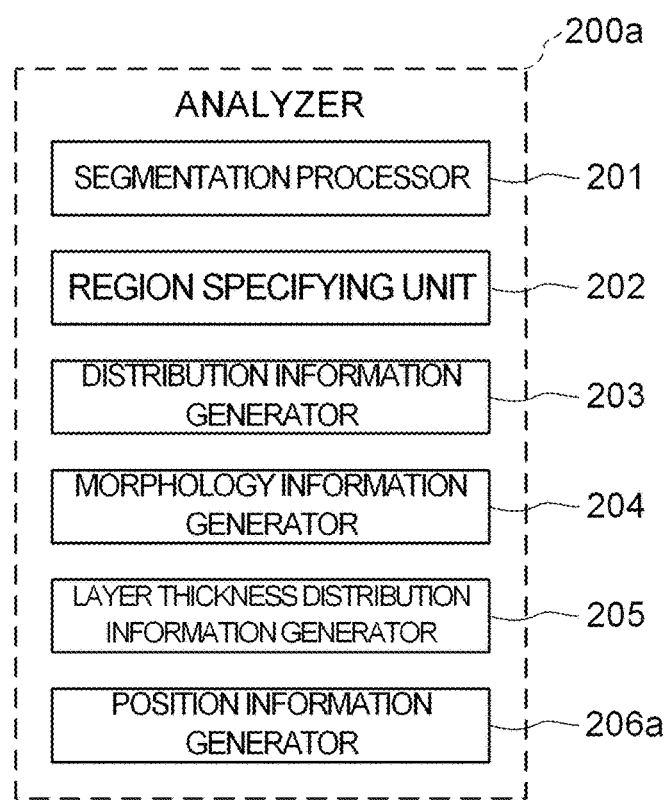
FIG. 15 is a schematic diagram illustrating an example of a configuration of the ophthalmologic information processing apparatus according to a modification example of the embodiments.

FIG. 15 shows a block diagram of an example of the configuration of the analyzer 200a according to the modification example of the embodiments. In FIG. 15, parts similar to those in FIG. 4 are denoted by the same reference symbols, and description thereof is omitted as appropriate.

In the present modification example, an analyzer 200a according to the modification example shown in FIG. 15 is provided instead of the analyzer 200 in the data processor 130 shown in FIG. 3. The analyzer 200a differs from the analyzer 200 in that a position information generator 206a is added to the analyzer 200.

The analyzer 200a specifies a region corresponding to the fovea by analyzing three-dimensional OCT data of the subject's eye using a known method, and specifies a region having a predetermined radius around the fovea as the macular region.

The position information generator 206a generates the position information. The position information represents a relative position of a representative position of the geographic atrophy region with respect to a representative position of the macular region specified by the analyzer 200a, a distance between both the representative positions, vector information indicating a movement direction or a movement distance of the representative position of the geographic atrophy region in a predetermined period, or vector information indicating a movement direction or a movement distance of the representative position of the geographic atrophy region with respect to the representative position of the macular region in a predetermined period. Examples of the representative position of the macular region include a position of the fovea, a position of the center of gravity of the macular region, the closest (or farthest) position to the geographic atrophy region in the outline of the macular region, and the like. Examples of the representative position of the geographic atrophy region include a center position of the geographic atrophy region, a position of the center of gravity of the geographic atrophy region, the closest (or farthest) position to the macular region (or the fovea) in the outline of the geographic atrophy region, and the like. The display controller 111A according to the modification example of some embodiments causes the position information, which is generated by the position information generator 206a, to be displayed on the display apparatus 190 in association with the geographic atrophy region corresponding to the position information.

Figure 16:
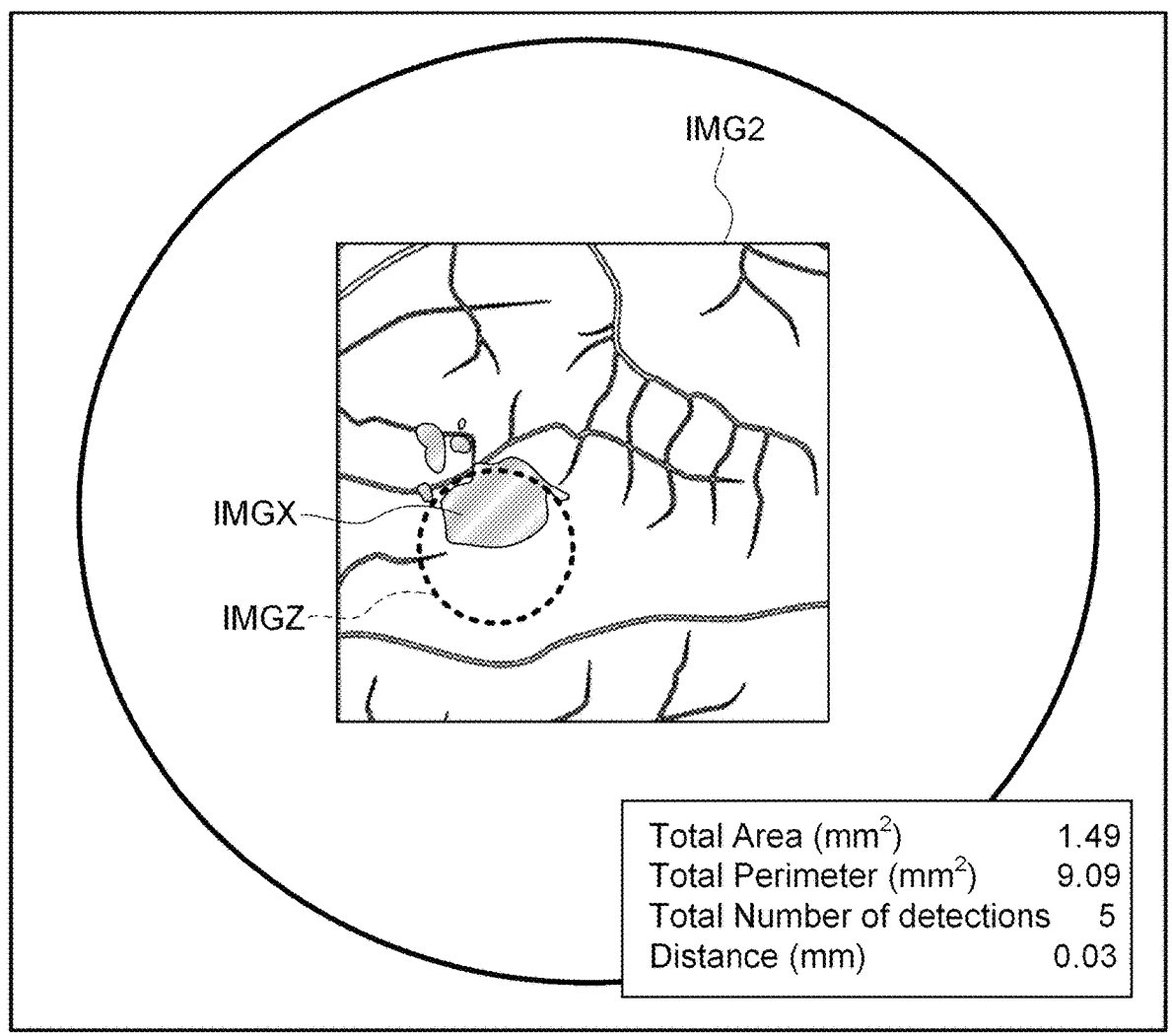
FIG. 16 is a schematic diagram for explaining an operation of the ophthalmologic information processing apparatus according to a modification example of the embodiments.

FIG. 16 shows an example of the analysis information displayed on the display apparatus 190 in the modification example of the embodiments.

For example, the display controller 111A causes the image IMGX representing the geographic atrophy region and the image IMGZ representing the position (range) of the macular region specified by the analyzer 200a superimposed on the shadowgram (the front image of the fundus) IMG2 to be displayed on the display apparatus 190. The image IMGZ may be an image representing a position of the fovea.

Further, the display controller 111A can cause the position information representing the relative position of the geographic atrophy region with respect to the macular region, in addition to the morphology information including the total value of the area(s) of the geographic atrophy region(s), the total value of the outer perimeter(s) of the geographic atrophy region(s), or the number of the geographic atrophy region(s) to be displayed on the display apparatus 190. The display controller 111A according to some embodiments causes the position information of each of the geographic atrophy regions to be displayed on the display apparatus 190 in association with the geographic atrophy region corresponding to the position information. Thereby, the position of each of the geographic atrophy regions can be observed in detail.

Figure 17:
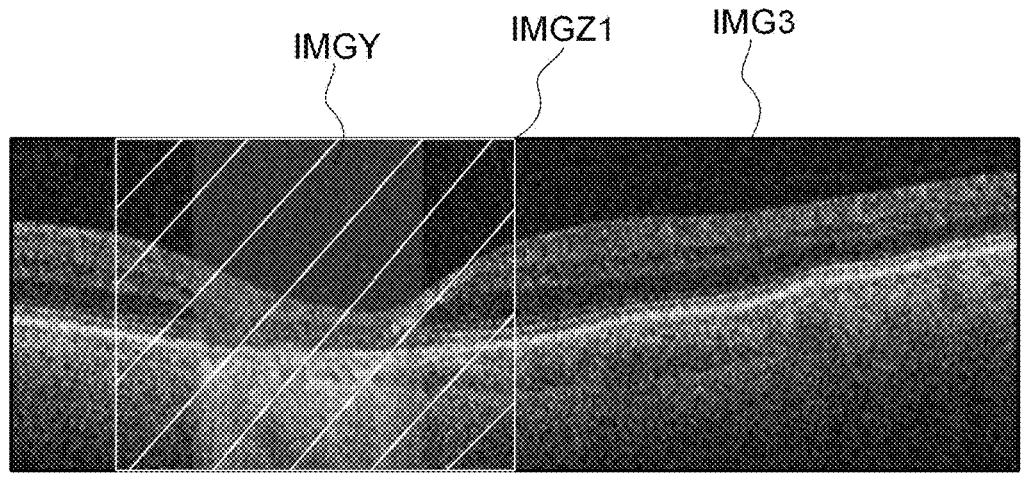
FIG. 17 is a schematic diagram for explaining an operation of the ophthalmologic information processing apparatus according to a modification example of the embodiments.

FIG. 17 shows another example of the analysis information displayed on the display apparatus 190 in the modification example of the embodiments.

For example, the display controller 111A causes the image IMGY representing the geographic atrophy region and the image IMGZ1 representing the position (range) of the macular region specified by the analyzer 200a superimposed on the B scan image IMG3 of the fundus to be displayed on the display apparatus 190. Thereby, the position of geographic atrophy region with respect of the macular region can be observed in the B scan image in detail.

Second Modification Example

The ophthalmologic apparatus according to some embodiments has at least one of the function of the ophthalmologic information processing apparatus 100, the function of the operating apparatus 180, and the function of the display apparatus 190, in addition to the function of the ophthalmologic apparatus 10.

In the following, the ophthalmologic apparatus according to a modification example of some embodiments will be described focusing on differences from the ophthalmologic apparatus according to the above embodiments.

Figure 18:
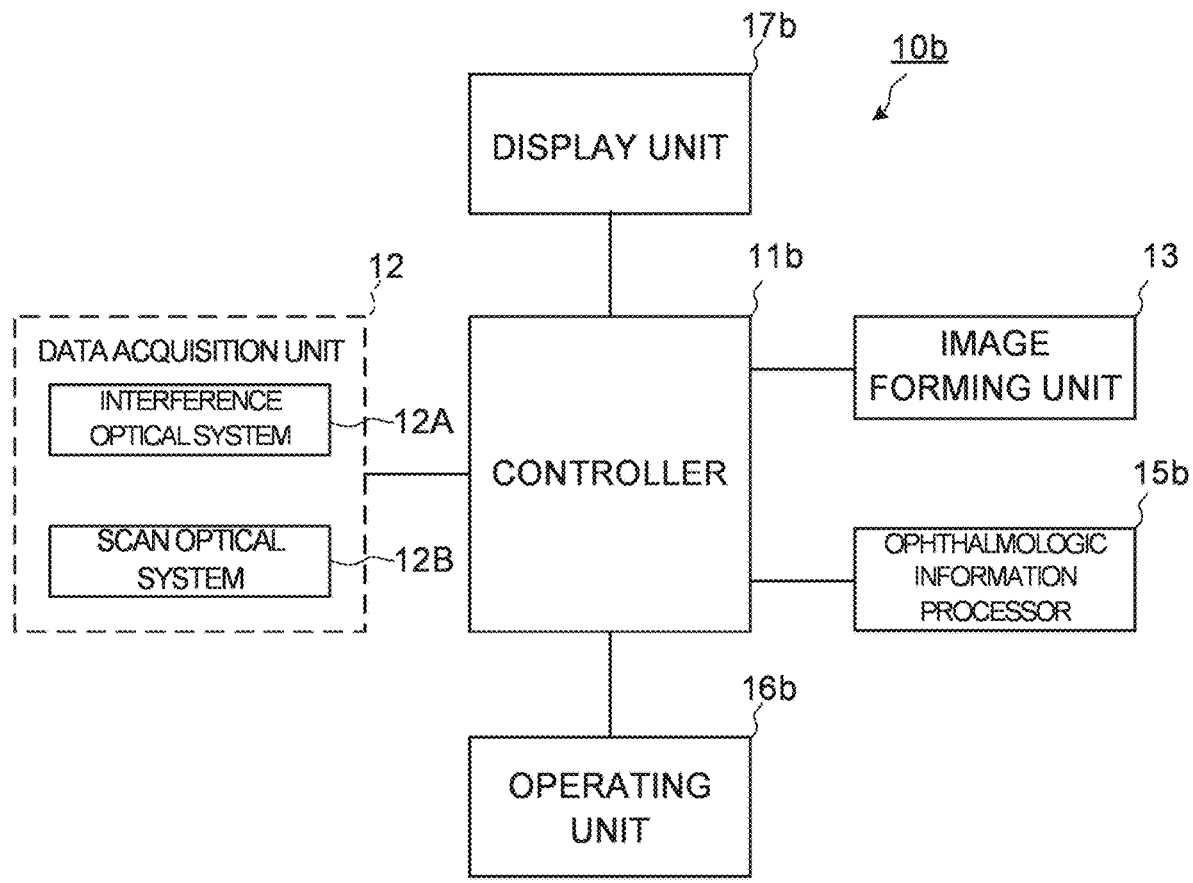
FIG. 18 is a schematic diagram illustrating an example of the configuration of the ophthalmologic apparatus according to a modification example of the embodiments.

FIG. 18 shows a block diagram of an example of the configuration of the ophthalmologic apparatus 10b according to the modification example of the embodiments. In FIG. 18, components similar to those in FIG. 2 are given the same reference numerals. The description of such components is basically omitted.

The difference between the configuration of the ophthalmologic apparatus 10b according to the present modification example and the configuration of ophthalmologic apparatus 10 according to the above embodiments is that the ophthalmologic apparatus 10b has the function of the ophthalmologic information processing apparatus 100, the function of the operating apparatus 180, and the function of the display apparatus 190. The ophthalmologic apparatus 10b includes a controller 11b, the data acquisition unit 12, the image forming unit 13, an ophthalmologic information processor 15b, an operating unit 16b, and a display unit 17b.

The controller 11b controls each part of the ophthalmologic apparatus 10b. In particular, the controller 11b controls the data acquisition unit 12, the image forming unit 13, the ophthalmologic information processor 15b, the operating unit 16b, and the display unit 17b.

The ophthalmologic information processor 15b has the same configuration as the ophthalmologic information processing apparatus 100, and has the same function as the ophthalmologic information processing apparatus 100. The operating unit 16b has the same configuration as the operating apparatus 180, and has the same function as the operating apparatus 180. The display unit 17b has the same configuration as the display apparatus 190, and has the same function as the display apparatus 190.

According to the present modification example, an ophthalmologic apparatus capable of observing in detail the morphology and the distribution of the geographic atrophy region in a compact configuration can be provided.

<Effects>

Hereinafter, the effects of the ophthalmologic information processing apparatus, the ophthalmologic system, the ophthalmologic information processing method, and the program according to some embodiments will be described.

An ophthalmologic information processing apparatus (100) according to some embodiments includes an analyzer (200, 200a), a storage unit (112), and a display controller (111A). The analyzer is configured to specify an atrophy region (geographic atrophy region) in a fundus by analyzing data of the fundus of a subject's eye acquired using optical coherence tomography. The storage unit stores image data of the fundus. The display controller is configured to cause a fundus image of the subject's eye based on the image data stored in the storage unit to be displayed on a display means (display apparatus 190), and to cause a region corresponding to the atrophy region in the fundus image to be displayed on the display means so as to be identifiable.

According to such a configuration, the fundus image of the subject's eye is displayed on the display means and the atrophy region in the fundus image is displayed so as to be identifiable. Thereby, the morphology or the distribution of the atrophy region such as a geographic atrophy region specified using optical coherence tomography can be observed in detail.

In the ophthalmologic information processing apparatus according to some embodiments, the analyzer includes a segmentation processor (201) and a distribution information generator (203). The segmentation processor is configured to specify a plurality of layer regions in an A scan direction based on the data of the fundus of the subject's eye. The distribution information generator is configured to generate distribution information (contrast map) on ratio between integrated values of pixel values in the A scan direction of the layer regions located on a sclera side with reference to a Bruch membrane and integrated values of pixel values in the A scan direction of the layer regions located on a cornea side with reference to the Bruch membrane. The analyzer is configured to specify the atrophy region based on the distribution information.

According to such a configuration, the atrophy region such as a geographic atrophy region from the data acquired using optical coherence tomography is specified and the specified atrophy region is displayed so as to be identifiable. Thereby, the morphology or the distribution of the atrophy region can be observed in detail while reducing the burden on the subject.

The ophthalmologic information processing apparatus according to some embodiments includes a position matching processor (210). The position matching processor is configured to perform position matching between the fundus image and an image representing the atrophy region specified based on the distribution information. The display controller is configured to cause the fundus image, on which the image representing the atrophy region is overlaid, to be displayed on the display means, the image having been performed position matching by the position matching processor.

According to such a configuration, the image representing the atrophy region such as a geographic atrophy region is overlaid on the fundus image. Thereby, the morphology or the distribution of the atrophy region on the fundus can be easily grasped, and accurate diagnosis of the atrophic AMD can be assisted.

In the ophthalmologic information processing apparatus according to some embodiments, the analyzer includes a morphology information generator (204). The morphology information generator is configured to generate morphology information representing morphology of the atrophy region by analyzing the data of the fundus of the subject's eye. The display controller is configured to cause the morphology information to be displayed on the display means.

According to such a configuration, the morphology of the atrophy region such as a geographic atrophy region can be easily grasped, and the morphology of each of the atrophy regions can be observed in detail. The display controller may cause the morphology information to be displayed on the display means in association with the atrophy region corresponding to the morphology information.

In the ophthalmologic information processing apparatus according to some embodiments, the morphology information includes at least one of an area of the atrophy region and an outer perimeter of the atrophy region.

According to such a configuration, the morphology of the atrophy region is represented with the area or the outer perimeter. Thereby, the morphology of the atrophy region can be observed quantitatively and in detail.

In the ophthalmologic information processing apparatus according to some embodiments, the display controller is configured to cause at least one of the area of the atrophy region and the outer perimeter of the atrophy region for each of the plurality of atrophy regions specified by the analyzer to be displayed on the display means.

According to such a configuration, the morphology of the atrophy region such as a geographic atrophy region can be easily grasped, and the morphology of each of the atrophy regions can be observed in detail.

In the ophthalmologic information processing apparatus according to some embodiments, the morphology information includes a total value of the areas of the plurality of atrophy regions specified by the analyzer or a total value of the outer perimeters of the plurality of atrophy regions specified by the analyzer.

According to such a configuration, the morphology or the distribution of the atrophy region can be observed quantitatively and in detail.

In the ophthalmologic information processing apparatus according to some embodiments, the morphology information includes number of the atrophy regions.

According to such a configuration, the morphology or the distribution of the atrophy region can be observed quantitatively and in detail.

In the ophthalmologic information processing apparatus according to some embodiments, the analyzer includes a position information generator (206a). The position information generator is configured to generate position information representing a position or a distance of the atrophy region with respect to a macular region in the fundus by analyzing the data of the fundus. The display controller is configured to cause the position information to be displayed on the display means.

According to such a configuration, the progress of the atrophic AMD can be easily grasped. Thereby, an accurate diagnosis of progressive atrophic AMD can be assisted. The display controller may cause the position information to be displayed on the display means in association with the atrophy region corresponding to the position information.

In the ophthalmologic information processing apparatus according to some embodiments, the analyzer is configured to specify a position of the macular region in the fundus based on the data of the fundus, and the display controller is configured to cause the fundus image, on which the image representing the position of the macular region is overlaid, to be displayed on the display means, the image being specified by the analyzer.

According to such a configuration, the progress of the atrophy AMD can be easily grasped. Thereby, an accurate diagnosis of progressive atrophic AMD can be assisted.

In the ophthalmologic information processing apparatus according to some embodiments, the fundus image is a shadowgram of a range from a retinal pigment epithelium layer to the Bruch membrane generated based on the data, a fluorescent fundus angiogram obtained by photographing the fundus, a fundus photographic image obtained by photographing the fundus, a projection image, or a C scan image.

According to such a configuration, the front image of the fundus of the subject's eye such as a shadowgram is displayed on the display means and the atrophy region in the front image is displayed so as to be identifiable. Thereby, the morphology or the distribution of the atrophy region such as a geographic atrophy region can be observed in detail.

In the ophthalmologic information processing apparatus according to some embodiments, the display controller is configured to cause a tomographic image of the fundus formed based on the data of the fundus as the fundus image to be displayed on the display means, and to cause a region corresponding to the atrophy region in the tomographic image to be displayed on the display means so as to be identifiable.

According to such a configuration, the tomographic image of the fundus of the subject's eye is displayed on the display means and the atrophy region in the fundus image is displayed so as to be identifiable. Thereby, the morphology or the distribution of the atrophy region such as a geographic atrophy region can be observed in detail.

An ophthalmologic system (1) according to some embodiments includes a data acquisition unit (12), the display means (display apparatus 190), and the ophthalmologic information processing apparatus described in any one of the above. The data acquisition unit is configured to acquire the data by scanning the subject's eye using optical coherence tomography.

According to such a configuration, the atrophy region in the fundus image of the subject's eye is displayed so as to be identifiable. Thereby, the ophthalmologic system capable of observing the morphology or the distribution of the atrophy region such as a geographic atrophy region in detail can be provided.

An ophthalmologic information processing method includes an analysis step and a display step. The analysis step is performed to specify an atrophy region (geographic atrophy region) in a fundus by analyzing data of the fundus of a subject's eye acquired using optical coherence tomography. The display step is performed to cause a fundus image of the subject's eye to be displayed on a display means (display apparatus 190) based on the image data of the fundus, and to cause a region corresponding to the atrophy region in the fundus image to be displayed on the display means so as to be identifiable.

According to such a configuration, the fundus image of the subject's eye is displayed on the display means and the atrophy region in the fundus image is displayed so as to be identifiable. Thereby, the morphology or the distribution of the atrophy region such as a geographic atrophy region specified using optical coherence tomography can be observed in detail.

In the ophthalmologic information processing method according to some embodiments, the analysis step includes a segmentation processing step and a distribution information generating step. The segmentation processing step is performed to specify a plurality of layer regions in an A scan direction based on the data. The distribution information generating step is performed to generate distribution information (contrast map) on ratio between integrated values of pixel values in the A scan direction of the layer regions located on a sclera side with reference to a Bruch membrane and integrated values of pixel values in the A scan direction of the layer regions located on a cornea side with reference to the Bruch membrane, the layer regions being specified in the segmentation processing step. The analysis step is performed to specify the atrophy region based on the distribution information.

According to such a configuration, the atrophy region such as a geographic atrophy region is specified from the data acquired using optical coherence tomography and the specified atrophy region is displayed so as to be identifiable. Thereby, the morphology or the distribution of the atrophy region can be observed in detail while reducing the burden on the subject.

The ophthalmologic information processing method according to some embodiments includes a position matching step. The position matching step is performed to perform position matching between the fundus image and the atrophy region specified based on the distribution information. The display step is performed to cause the fundus image, on which the image representing the atrophy region is overlaid, to be displayed on the display means, the image having been performed position matching in the position matching step.

According to such a configuration, the image representing the atrophy region such as a geographic atrophy region is overlaid on the fundus image. Thereby, the morphology or the distribution of the atrophy region on the fundus can be easily grasped, and accurate diagnosis of the atrophic AMD can be assisted.

In the ophthalmologic information processing method according to some embodiments, the analysis step includes a morphology information generating step. The morphology information generating step is performed to generate morphology information representing morphology of the atrophy region by analyzing the data of the fundus. The display step is performed to cause the morphology information to be displayed on the display means.

According to such a configuration, the morphology of the atrophy region such as a geographic atrophy region can be easily grasped, and the morphology of the atrophy region can be observed in detail.

In the ophthalmologic information processing method according to some embodiments, the morphology information includes at least one of an area of the atrophy region, an outer perimeter of the atrophy region.

According to such a configuration, the morphology of the atrophy region is represented with the area or the outer perimeter. Thereby, the morphology of the atrophy region can be observed quantitatively and in detail.

In the ophthalmologic information processing method according to some embodiments, the display step is performed to cause at least one of the area of the atrophy region and the outer perimeter of the atrophy region to be displayed on the display means for each of the plurality of atrophy regions specified in the analysis step.

According to such a configuration, the morphology of the atrophy region such as a geographic atrophy region can be easily grasped, and the morphology of each of the atrophy regions can be observed in detail.

A program according to some embodiments causes a computer to execute each step of the ophthalmologic information processing method described in any of the above.

According to such a configuration, the computer causes the atrophy region in the fundus image of the subject's eye to display so as to be identifiable. Thereby, the program for observing the morphology or the distribution of the atrophy region such as a geographic atrophy region in detail can be provided.

A program for realizing the ophthalmologic information processing method according to some embodiments can be stored in any kind of computer non-transitory recording medium. The recording medium may be an electronic medium using magnetism, light, magneto-optical, semiconductor, or the like. Typically, the recording medium is a magnetic tape, a magnetic disk, an optical disk, a magneto-optical disk, a flash memory, a solid state drive, or the like.

The computer program may be transmitted and received through a network such as the Internet, LAN, etc.

Configurations described above are merely examples for preferably implementing the present invention. One who intends to implement the present invention may arbitrarily modify (omission, replacement, addition, etc.) within the scope of the invention.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic information processing apparatus, comprising:
    processing circuitry that specifies an atrophy region in a fundus by analyzing data of the fundus of a subject's eye acquired using optical coherence tomography;
    a storage memory storing image data of the fundus;
    the processing circuitry generates position information representing vector information indicating a movement direction and a movement distance of a representative position of the atrophy region with respect to a representative position of a macular region in a predetermined period by analyzing the data, the representative position of the macular region including one of a position of the fovea, a position of a center of gravity of the macular region, a closest position to the atrophy region in an outline of the macular region, and a farthest position to the atrophy region in the outline of the macular region, the representative position of the atrophy region including one of a center position of the atrophy region, a position of a center of gravity of the atrophy region, a closest position to the macular region or the fovea in an outline of the atrophy region, or a farthest position to the macular region or the fovea in the outline of the atrophy region; and a display controller that causes a fundus image of the subject's eye to be displayed on a display based on the image data stored in the storage memory, to cause a region corresponding to the atrophy region in the fundus image to be displayed on the display so as to be identifiable, and to cause the generated position information to be displayed on the display.

2. The ophthalmologic information processing apparatus of claim 1, wherein the analyzer includes:

a segmentation processor that specifies a plurality of layer regions in an A scan direction based on the data, and a distribution information generator that generates distribution information on ratio between integrated values of pixel values in the A scan direction of the layer regions located on a sclera side with reference to a Bruch membrane and integrated values of pixel values in the A scan direction of the layer regions located on a cornea side with reference to the Bruch membrane, the layer regions being specified by the segmentation processor, and the analyzer specifies the atrophy region based on the distribution information.

3. The ophthalmologic information processing apparatus of claim 2, further comprising a position matching processor that performs position matching between the fundus image and an image representing the atrophy region specified based on the distribution information, wherein the display controller causes the fundus image, on which the image representing the atrophy region is overlaid, to be displayed on the display, the image having been performed position matching by the position matching processor.

4. The ophthalmologic information processing apparatus of claim 1, wherein the analyzer includes a morphology information generator that generates morphology information representing morphology of the atrophy region by analyzing the data, and the display controller causes the morphology information to be displayed on the display.

5. The ophthalmologic information processing apparatus of claim 4, wherein the morphology information includes at least one of an area of the atrophy region and an outer perimeter of the atrophy region.

6. The ophthalmologic information processing apparatus of claim 5, wherein the display controller causes at least one of the area of the atrophy region and the outer perimeter of the atrophy region to be displayed on the display for each of the plurality of atrophy regions specified by the analyzer.

7. The ophthalmologic information processing apparatus of claim 6, wherein the morphology information includes a total value of the areas of the plurality of atrophy regions specified by the analyzer or a total value of the outer perimeters of the plurality of atrophy regions specified by the analyzer.

8. The ophthalmologic information processing apparatus of claim 4, wherein the morphology information includes number of the atrophy regions.

9. The ophthalmologic information processing apparatus of claim 1, wherein the analyzer specifies a position of the macular region in the fundus based on the data, and the display controller causes the fundus image, on which the image representing the position of the macular region is overlaid, to be displayed on the display, the image being specified by the analyzer.

10. The ophthalmologic information processing apparatus of claim 1, wherein the fundus image is a shadowgram of a range from a retinal pigment epithelium layer to the Bruch membrane generated based on the data, a fluorescent fundus angiogram obtained by photographing the fundus, a fundus photographic image obtained by photographing the fundus, a projection image, or a C scan image.

11. The ophthalmologic information processing apparatus of claim 1, wherein the display controller causes a tomographic image of the fundus formed based on the data as the fundus image to be displayed on the display, and a region corresponding to the atrophy region in the tomographic image to be displayed on the display so as to be identifiable.

12. An ophthalmologic system, comprising:

a data acquisition unit including a scanner that acquires the data by scanning the subject's eye using optical coherence tomography;

the display; and the ophthalmologic information processing apparatus according to claim 1.

13. The ophthalmologic information processing apparatus of claim 1, wherein the atrophy region is a geographic atrophy region.

14. The ophthalmologic information processing apparatus of claim 1, wherein the position information of the atrophy region is displayed on the display in association with the atrophy region corresponding to the position information.

15. An ophthalmologic information processing method, comprising:

specifying an atrophy region in a fundus by analyzing data of the fundus of a subject's eye acquired using optical coherence tomography;

generating position information representing vector information indicating a movement direction and a movement distance of a representative position of the atrophy region with respect to a representative position of a macular region in a predetermined period by analyzing the data, the representative position of the macular region including one of a position of the fovea, a position of a center of gravity of the macular region, a closest position to the atrophy region in an outline of the macular region, and a farthest position to the atrophy region in the outline of the macular region, the representative position of the atrophy region including one of a center position of the atrophy region, a position of a center of gravity of the atrophy region, a closest position to the macular region or the fovea in an outline of the atrophy region, or a farthest position to the macular region or the fovea in the outline of the atrophy region;

causing a fundus image of the subject's eye to be displayed on a display based on the image data of the fundus;

causing a region corresponding to the atrophy region in the fundus image to be displayed on the display so as to be identifiable; and causing the generated position information to be displayed on the display.

16. The ophthalmologic information processing method of claim 15, wherein
the specifying the atrophy region includes:
specifying a plurality of layer regions in an A scan direction based on the data,
generating distribution information on ratio between integrated values of pixel values in the A scan direction of the layer regions located on a sclera side with reference to a Bruch membrane and integrated values of pixel values in the A scan direction of the layer regions located on a cornea side with reference to the Bruch membrane, the layer regions being specified in the segmentation processing step, and
specifying the atrophy region based on the distribution information.

17. The ophthalmologic information processing method of claim 16, further comprising
performing position matching between the fundus image and the atrophy region specified based on the distribution information, wherein
the causing the fundus image of the subject's eye to be displayed is performed to cause the fundus image, on which the image representing the atrophy region is overlaid, to be displayed on the display, the image having been position matched in the performing position matching.

18. The ophthalmologic information processing method of claim 15, further comprising:
generating morphology information representing morphology of the atrophy region by analyzing the data, and
causing the morphology information to be displayed on the display.

19. The ophthalmologic information processing method of claim 18, wherein
the morphology information includes at least one of an area of the atrophy region, an outer perimeter of the atrophy region.

20. The ophthalmologic information processing method of claim 19, further comprising:
causing at least one of the area of the atrophy region and the outer perimeter of the atrophy region to be displayed on the display for each of the plurality of atrophy regions specified in the analysis step.

21. A non-transitory computer readable recording medium storing a program of causing a computer to execute each step of an ophthalmologic information processing method comprising:
specifying an atrophy region in a fundus by analyzing data of the fundus of a subject's eye acquired using optical coherence tomography;
generating position information representing vector information indicating a movement direction and a movement distance of a representative position of the atrophy region with respect to a representative position of a macular region in a predetermined period by analyzing the data, the representative position of the macular region including one of a position of the fovea, a position of a center of gravity of the macular region, a closest position to the atrophy region in an outline of the macular region, and a farthest position to the atrophy region in the outline of the macular region, the representative position of the atrophy region including one of a center position of the atrophy region, a position of a center of gravity of the atrophy region, a closest position to the macular region or the fovea in an outline of the atrophy region, or a farthest position to the macular region or the fovea in the outline of the atrophy region;
causing a fundus image of the subject's eye to be displayed on a display based on the image data of the fundus;
causing a region corresponding to the atrophy region in the fundus image to be displayed on the display so as to be identifiable; and
causing the generated position information to be displayed on the display.

* * * * *